United States Patent [19]

Drucker

[11] Patent Number: 6,051,557
[45] Date of Patent: Apr. 18, 2000

[54] METHODS OF ENHANCING FUNCTIONING OF THE UPPER GASTROINTESTINAL TRACT

[75] Inventor: Daniel J. Drucker, Ontario, Canada

[73] Assignee: 1149336 Ontario Inc., Toronto, Canada

[21] Appl. No.: 09/059,504

[22] Filed: Apr. 13, 1998

Related U.S. Application Data

[60] Provisional application No. 60/046,754, May 16, 1997.

[51] Int. Cl.[7] ................................................ A61K 38/00
[52] U.S. Cl. .......................... 514/12; 530/308; 530/324; 435/366; 935/52; 935/55
[58] Field of Search ............................. 514/12; 530/308, 530/324; 435/366; 935/52, 55

[56] References Cited

U.S. PATENT DOCUMENTS

| | | | |
|---|---|---|---|
| 5,288,703 | 2/1994 | Wilmore | 514/2 |
| 5,482,926 | 1/1996 | Gluckman et al. | 514/12 |
| 5,834,428 | 11/1998 | Drucker | 514/12 |

FOREIGN PATENT DOCUMENTS

| | | |
|---|---|---|
| 612531 | 8/1994 | European Pat. Off. . |
| WO 97/31943 | 9/1997 | WIPO . |

OTHER PUBLICATIONS

Drucker et al., *Proc. Natl. Acad. Sci. USA*, vol. 93, pp. 7911–7916, 1996.

Hcaplus AN 1994: 672947, Read et al., *Int. Congr. Ser.—Excerpta Med.*, 1056, 409–416. (Abstract) 1994.

Dayhoff, *Atlas of Protein Sequence and Structure*, vol. 5, p. 96, 1972.

Barragán et al., 1994, "Changes in arterial blood pressure and heart rate induced by glucagon–like peptide–1(7–36) amide in rats," *American Journal of Physiology* 266(3 Pt 1):E459–66.

Barragán et al., 1996, "Interactions of exendin–(9–39) with the effects of glucagon–like peptide–1–(7–36) amide and of exendin–4 on arteria blood pressure and heart rate in rats," *Regulatory Peptides* 67:63–68.

Bloom, 1987, "Gut Hormones in adaptation," *Gut.* 28(S1):31–35.

Brubaker, 1991, "Regulation of Intestinal Proglucagon–Derived Peptide Secreation by Intestinal Regulatory Peptides," *Endocrinology.* 128(6):3175–3182.

Brubaker, 1997, "Intestinal function in mice with small bowel growth induced by glucagon–like peptide–2," *Am. J. Physiol.* 272:E1050–E1058.

Buhl et al., 1988, "Naturally Occurring Products of Proglucagon 111–160 in the Porcine and Human Small Intestine," *The Journal of Biological Chemistry* 263(No.18):8621–8624.

Calvo et al, 1995, "Structural characterization by affinity cross–linking of glucagon–like peptide–1 (7–36) amide receptor in rat brain," *J. Neurochem.* 64(1):299–306.

Cheeseman et al., 1966, "Thei effect of gastric inhibitory polypeptide and glucagon like peptides on intestin basolateral membrane hexose transport," *The American Physiological Society* APSracts 3:0071G.

Cheeseman, 1997, "Upregulation of SGLT–1 transport activity in rat jejunum induced by GLP–2 infusion in vivo," *American Physiological Society* pp. R1965–R1971.

Drucker, 1990, "Glucagon and the glucagon–like peptides", *Pancreas.* 5(4):484.

Drucker et al, 1997, "Regulation of the biological activity of glucagon–like peptide 2 in vivo by dipenptidyl peptidaseIV," *Nature Biotechnology* 15:673–677.

Ehrlich et al., 1994, "Inhibition of pancreatic proglucagon gene expression in mice bearing subcutaneous endocrine tumors," *American Journal of Physiology* pp.E662–E671.

George et al, 1985, "Molecular forms of glucagon–lke peptides in man," *FEBS Letters* 192(2):275–278.

Hoosein et al., 1984, "Human glucagon–like peptides 1 and 2 activate rat brain adenylate cyclase," *FEBS Letters* 178(1):83–86.

Irwin et al., 1995, "Trout and Chicken Proglucagon: Alternative Splicing Generates mRNA Transcripts Encoding Glucagon–Like Peptide 2," *Molecular Endocrinology* 9:267–277.

Lee et al., 1992, "Glucagon Gene 5'–Flanking Sequences Direct Expression of Simian Virus 40 Large T Antigen to the Intestine, Producing Carcimona of the Large Bowl in Transgenic Mice," *The Journal of Biological Chemistry* 267:(15):10706–10708.

Litvak et al., 1997, "Glucagon–like Peptide 2: A Potent Intestinal Growth Factor," *Gastroenterolgy* 112(4 Suppl.):A1455.

Lund et al., 1993, "Regulation of Intestinal Glucagon Gene Expression during Adaptive Growth of Small Intestine," *Digestion* 54:371–373.

(List continued on next page.)

*Primary Examiner*—Cecilia J. Tsang
*Assistant Examiner*—C. Delacroix-Muirheid
*Attorney, Agent, or Firm*—Pennie & Edmonds LLP

[57] ABSTRACT

The invention relates to glucagon-related peptides and their use for the prevention or treatment of disorders involving the upper gastrointestinal tract including the esophagus and stomach. In particular, it has now been demonstrated that GLP-2 and peptidic agonists of GLP-2 can cause proliferation of the tissue of the upper gastrointestinal tract. Thus, the invention provides methods of proliferating the upper gastrointestinal tract in a subject in need thereof. Further, the methods of the invention are useful to treat or prevent inflammatory conditions of the upper gastrointestinal tract, including inflammatory diseases. GLP-2 stimulates the growth of upper gastrointestinal tissue when administered in conjunction with other peptide hormones. The invention further provides pharmaceutical compositions of GLP-2 with at least one other peptide hormone, methods of enhancing the growth of upper gastrointestinal tissue and of gastrointestinal disorders by increasing serum levels of GLP-2 and at least one other peptide hormone, and kits for preforming the methods of the invention.

48 Claims, 2 Drawing Sheets

OTHER PUBLICATIONS

Mojsov et al., 1986, "Preproglucagon Gene Expression in Pancreas and Intestine Diversifies at the Level of Post–translational Processing," *The Journal of Biological Chemistry* 261(25):1180–11889.

Mommsen et al, 1987, "Glucagon–like peptides activate hepatic gluconeogenesis," *FEBS Letters* 219(1):227–232.

Nishi et al., 1990, "Cloning of complementary DNAs encoding islet amyloid polypeptide, insulin, glucagon precursors from a new world rodent, the degu, Octodon degus" *Mol. Endocrinol.* 4:1192–8.

Orskov et al., 1989, "Carboxypeptidase–B–like processing of the C–terminus of glucagon–like peptide–2 in pig and human small intestine," *FEBS* Letters 247(2):193–196.

Orskov et al., 1987, "Pancreatic and intestinal processing of proglucagon in man," *Diabetologia* 30:874–881.

Orskov et al., 1987, "Radio–immunoassays for glucagon–like peptides 1 and 2 (GLP–1) and GLP–2)," *Scand. J. Clin. Lab. Invest.* 47(2):165–174.

Orskov et al., 1986, "Glucagon–Like Peptides GLP–1 and GLP–2, Predicted Products of the Glucagon Gene, Are Secreted Separately from Pig Small Intestine but Not Pancreas," *Endocrinology* 119(4):1467–1475.

Ruiz–Grand et al, 1990, "Rental catabolism of human glucagon–like peptides 1 and 2," *Can. J. Physiol. Pharmacol.* 68(12):1568–1573.

Scrocchi et al., 1996, "glucose intolerance but normal satiety in mice with a null mutation in the glucagon–like peptide 1 receptor gene," *Nature Medicine* 2:1254–1258.

Shennan et al., 1989, "Proglucagon expression, posttranslational processing and secretion in SV40–transformed islet cells," *Molecular and Cellular Endocrinology* 67:93–99.

Singh et al., 1994 "Use of $^{126}$I–[Y$^{39}$]exendin–4 to characterize exendin receptors on dispersed pancreatic acini and gastric chief cells from guinea pig," *Regulatory Peptides* 53:47–59.

Tsai et al., 1997, "Biological determinants of intestinotrophic properties of GLP–2 in vivo," *Am. J. Physiol.* 272:G662–G668.

Watanabe et al., 1988, "Trophic Effect of Glucagon–(1–21)–Peptide on the Isolated Rat Ileal Mucosal Cells," *Biochemical and Biophysical Research Communications* 152(3):1038–1044.

6,051,557

METHODS OF ENHANCING FUNCTIONING OF THE UPPER GASTROINTESTINAL TRACT

This application claims benefit of provisional application Ser. No. 60/046,754, filed May 16, 1997.

FIELD OF INVENTION

This invention relates to glucagon-related peptides and their use, either alone or in combination with other peptide hormones, for the prevention or treatment of disorders involving the both the upper and lower gastrointestinal tract.

BACKGROUND OF THE INVENTION

Glucagon-like peptide-2 (GLP-2) is a 33 amino acid peptide expressed in a tissue-specific manner from the pleiotropic glucagon gene. GLP-2 shows remarkable homology in terms of amino acid sequence to glucagon and Glucagon-Like Peptide-1 (GLP-1). Further, different mammalian forms of GLP-2 are highly conserved. For example, the human GLP-2 and degu (a south American rodent) GLP-2 differ from rat GLP-2 by one and three amino acids respectively. When given exogenously, GLP-2 can produce a marked increase in the proliferation of small intestinal epithelium of test mice, apparently with no undesirable side effects (Drucker et al., 1996, *PNAS:USA* 93:7911–7916). Subsequently it was shown that peptide analogs of native GLP-2 with certain modifications to the peptide sequence possess enhanced trophic activity at the small intestine (see co-pending application U.S. Ser. No. 08/669,791, filed Jun. 28, 1996, incorporated herein by reference). It has further been demonstrated that GLP-2 can proliferate the tissue of the large intestine (co-pending applications U.S. Ser. No. 08/763,177, filed Dec. 10, 1996, and U.S. Ser. No. 08/850,664, filed on May 2, 1997, and Litvak et al., 1997, *Gastroenterology*, vol. 112 (4 Suppl.), page A1455, all of which are incorporated herein by reference). Moreover, GLP-2 has also been shown to increase D-glucose maximal transport rate across the intestinal basolateral membrane (Cheeseman and Tseng, 1996, *American Journal of Physiology* 271:G477-G482).

A number of peptide hormones, structurally unrelated to GLP-2, have been demonstrated to have varying degrees of trophic activity. For example, Insulin-Like Growth Factor-2 (IGF-2) has been shown to promote mitosis of the crypt cells of the small intestine in vivo (U.S. Pat. No. 5,482,926). Insulin-Like Growth Factor-1 (IGF-1), which shares 64% sequence identity with IGF-2, and peptide analogs thereof have also been shown to increase the growth of gut tissue in vivo (WO 91/12018). Growth Hormone (GH) has been shown to have a number of physiological effects, including increasing proliferation of the intestinal mucosa (see, for example, Willmore, U.S. Pat. No. 5,288,703), thereby enhancing the absorptive capacity of the gut. However, none of the above peptide hormones possess the efficacy or specificity of GLP-2 in promoting proliferation of the tissue of the lower gastrointestinal tract.

SUMMARY OF THE INVENTION

The invention is based, in part, on the discovery that GLP-2 receptor agonists act to enhance functioning of the upper gastrointestinal tract. Specifically, it has been demonstrated that GLP-2 can proliferate the tissue of the esophagus and stomach. It is accordingly a general object of the present invention to exploit GLP-2 receptor agonists for therapeutic and related purposes.

In particular, it has been demonstrated that GLP-2 and peptidic analogs of GLP-2 can cause proliferation of the tissue of upper gastrointestinal tract. Thus, one aspect the invention provides a method of proliferating the tissue of the upper gastrointestinal tract in a subject in need thereof comprising delivering to the upper gastrointestinal tract of the subject an upper gastrointestinal tract proliferating amount of GLP-2 or a GLP-2 analog.

In addition, it has been demonstrated that GLP-2 can ameliorate nonsteroidal anti-inflammatory drug (NSAID) induced gastrointestinal toxicity. Thus, the invention provides methods of therapeutically or prophylactically treating a subject with or at risk of an inflammatory condition of the gastrointestine involving the upper gastrointestinal tract, comprising delivering to the upper gastrointestinal tract an effective amount of GLP-2 or a GLP-2 analog.

More particularly, and according to one aspect of the invention, there is provided a method of treating a subject suffering from a condition involving the upper gastrointestinal tract, wherein GLP-2 or a GLP-2 analog is delivered to the upper gastrointestinal tract in an amount capable of ameliorating the condition.

In a related aspect of the invention, there is provided a method of treating a subject having a damaged, partially resected, eroded or inflamed esophagus comprising the step of delivering to the subject a upper gastrointestinal tract damage or inflammation ameliorating amount of GLP-2 or an analog of GLP-2 in a pharmaceutically or veterinarily acceptable carrier. In a further aspect, GLP-2 or a GLP-2 analog is provided in a pharmaceutically or veterinarily acceptable form in an amount effective to cause proliferation of the upper gastrointestinal tract.

In a further aspect of the invention, there is provided a method of treating a subject having a damaged, atrophic or inflamed stomach comprising the step of delivering to the subject a stomach damage or inflammation ameliorating amount of GLP-2 or an analog of GLP-2 in a pharmaceutically or veterinarily acceptable carrier. In a further aspect, GLP-2 is provided in a pharmaceutically or veterinarily acceptable form in an amount effective to cause proliferation of the tissue of the stomach.

In another aspect, the invention provides a method of prophylactically treating a subject at risk of developing an inflammatory condition of the gastrointestine involving the upper gastrointestinal tract comprising the steps of:
  a) identifying a subject at risk of developing an inflammatory condition involving the upper gastrointestinal tract; and
  b) administering to the subject an amount of GLP-2 or a GLP-2 analog effective to inhibit onset of the inflammatory condition.

In another aspect of the invention, there is provided a method to identify peptides useful to treat inflammatory conditions involving the upper gastrointestinal tract comprising the steps of:
  a) obtaining an analog of a vertebrate GLP-2 peptide, the analog having at least one amino acid substitution, deletion, addition, or an amino acid with a blocking group;
  b) inducing an inflammatory condition of the upper gastrointestinal tract in a test animal;
  c) treating the test animal having an induced inflammatory condition of the upper gastrointestinal tract with the analog using a regimen capable of eliciting an amelioration of the inflammatory condition of the upper gastrointestinal tract when utilized for human [Gly$^2$] GLP-2; and d) determining the effect of the analog on the health status or mortality of the test animal compared with control animals not receiving the peptide or determining the mass of the upper gastrointestinal tract of test animals compared to control animals not receiving peptide.

In another aspect of the invention, there is provided a method to identify peptides useful to prevent or ameliorate inflammatory conditions involving the upper gastrointestinal tract comprising the steps of:
  a) obtaining an analog of a vertebrate GLP-2 peptide, the analog having at least one amino acid substitution, deletion, addition, or an amino acid with a blocking group;
  b) treating a test animal with the analog using a regimen capable of eliciting an amelioration of the inflammatory condition of the upper gastrointestinal tract when utilized for human [Gly$^2$]GLP-2;
  c) inducing an inflammatory condition of the upper gastrointestinal tract in a test animal;
  e) determining the effect of the analog on the health status or mortality of the test animal compared with control animals not receiving the peptide or determining the mass of the upper gastrointestinal tract of test animals compared to control animals not receiving peptide.

In another aspect, the invention provides a method of prophylactically treating a subject at risk of developing an inflammatory condition of the gastrointestine involving the upper gastrointestinal tract comprising the steps of:
  a) identifying a subject at risk of developing an inflammatory condition involving the upper gastrointestinal tract; and
  b) administering to the subject an amount of GLP-2 or a GLP-2 analog effective to inhibit onset and/or ameliorate the development of the inflammatory condition.

In a related aspect of the invention, there is provided a method useful to identify peptides capable of proliferating the tissue of the upper gastrointestinal tract comprising the steps of:
  a) obtaining an analog of a vertebrate GLP-2 peptide, the analog having at least one amino acid substitution, deletion, addition, or an amino acid with a blocking group;
  b) delivering the analog to the upper gastrointestinal tract of the test animal using a regimen capable of proliferating the upper gastrointestinal tract when utilized for human [Gly$^2$]GLP-2; and
  c) assessing the increase in the mass, length, or total protein content of the upper gastrointestinal tract or a representative portion after completion of the treatment regime.

In another aspect, the invention provides a method for growing upper gastrointestinal tract tissue or cells therefrom, which comprises the step of culturing the tissue or cells in a culturing medium supplemented with a growth promoting amount of GLP-2 or a GLP-2 analog.

The invention is also based, in part, on the expectation that GLP-2 or a GLP-2 analog will act synergistically with the peptide hormones IGF-1 and/or GH to promote the proliferation of cells. Furthermore, coadministration of GLP-2 with either IGF-1 or GH results in cell proliferation. The trophic effects on the small and large intestines of this combination therapy are greater than that seen with any one of GLP-2, IGF-1 or GH alone. An additional aspect of the invention is the coadministration of GLP-2 with IGF-2 or GH to promote growth.

Therefore, one aspect of the invention is a composition for promoting the growth of upper gastrointestinal tract tissue in a mammal which comprises GLP-2, or a trophic analog of GLP-2, in admixture with at least one other peptide hormone selected from the group consisting of IGF-1, IGF-2, and GH, and a pharmaceutically acceptable carrier. These compositions of the invention may alternatively include analogs of GLP-2, IGF-1, IGF-2 and/or GH which exhibit trophic activities.

In another aspect, the invention provides a method of promoting the growth of upper gastrointestinal tract tissue in a mammal, comprising treating the mammal to elevate serum levels of GLP-2, or an analog of GLP-2, and at least one other peptide hormone selected from the group consisting of IGF-1, analogs of IGF-1, IGF-2, analogs of IGF-2, GH, and analogs of GH. Such methods of the invention include co-administering to a mammal an effective amount of GLP-2 and an effective amount of at least one other peptide hormone selected from the group consisting of IGF-1, analogs of IGF-1, IGF-2, analogs of IGF-2, GH, and analogs of GH, treating the mammal with hormones or small organic molecules which act to elevate serum levels of GLP-2, IGF-1, IGF-2, and/or GH, and performing gene therapy to induce cells in the mammal to endogenously produce GLP-2, IGF-1, IGF-2, and/or GH or to engineer cells to produce GLP-2, IGF-1, IGF-2, or GH, alone or in combination, that may then be implanted in a mammal to produce the desired biological effect.

Also provided by the invention is a method for treating a subject to enhance functioning of the upper gastrointestinal tract, comprising treating the mammal to elevate serum levels of GLP-2, or an analog of GLP-2, and at least one other peptide hormone selected from the group consisting of IGF-1, analogs of IGF-1, IGF-2, analogs of IGF-2, GH, and analogs of GH.

The compositions and methods of the invention are useful for restoring or maintaining gastrointestinal function, for promoting the healing and regrowth of injured or ulcerated/inflamed intestinal mucosa, for reducing the risk of enteric disease, for enhancing the nutritional status of a mammal, and for the treatment or prevention of nutritional or upper gastrointestinal disorders in a mammal, particularly a human.

Alternatively, the compositions and methods of the invention can be used to promote proliferation of the upper gastrointestinal tract in a healthy mammal, e.g., to enable increased absorption of nutrients in cattle allowing earlier weaning or increased milk and meat production.

In yet another aspect of the invention, there is provided a use of GLP-2, or analogs of GLP-2, for the manufacture of a pharmaceutical or veterinary preparation for the enhancement of upper gastrointestinal tract tissue growth. In a particularly preferred aspect of the invention, such preparations also include another peptide hormone selected from the group consisting of IGF-1, analogs of IGF-1, IGF-2, analogs of IGF-2, GH, and analogs of GH.

Still further, the invention provides kits comprising GLP-2, or analogs of GLP-2, and at least one other peptide hormone selected from the group consisting of IGF-1, analogs of IGF-1, IGF-2, analogs of IGF-2, GH, and analogs of GH. Such compositions are provided in a therapeutically effective unit dose or multi-dose amount.

Also provided by the instant invention is a method for promoting the growth of upper gastrointestinal tract tissue or cells which comprises the step of culturing said tissue or cells in a culturing medium containing a growth promoting combination of both GLP-2, or a GLP-2 analog, and at least one other peptide hormone selected from the group consisting of IGF-1, analogs of IGF-1, IGF-2, analogs of IGF-2, GH, and analogs of GH. These methods may be performed on cells in culture and in vivo.

In yet another aspect of the invention, there is provided a method in which treatment of a patient to restore upper gastrointestinal tract tissue is performed by the steps of: (a) culturing tissue or cells derived from the patient with a tissue growth promoting amount of a combination of GLP-2 or an GLP-2 analog, and at least one other peptide hormone selected from the group consisting of IGF-1, analogs of IGF-1, IGF-2, analogs of IGF-2, GH, and analogs of GH, and then (b) implanting said tissue or cells in the patient to be treated.

Finally, the invention also provides a method for determining the activity of a hormone when used in combination with GLP-2 which comprises the steps of: (1) coadministering the hormone with an amount of GLP-2, or a GLP-2 analog, to a test mammal; (2) assessing the subsequent growth of upper gastrointestinal tract tissue in the test mammal; and (3) determining whether the growth of upper gastrointestinal tract tissue in the test mammal is enhanced relative to control mammals treated with GLP-2 alone.

DETAILED DESCRIPTION OF THE INVENTION

Figure 1:
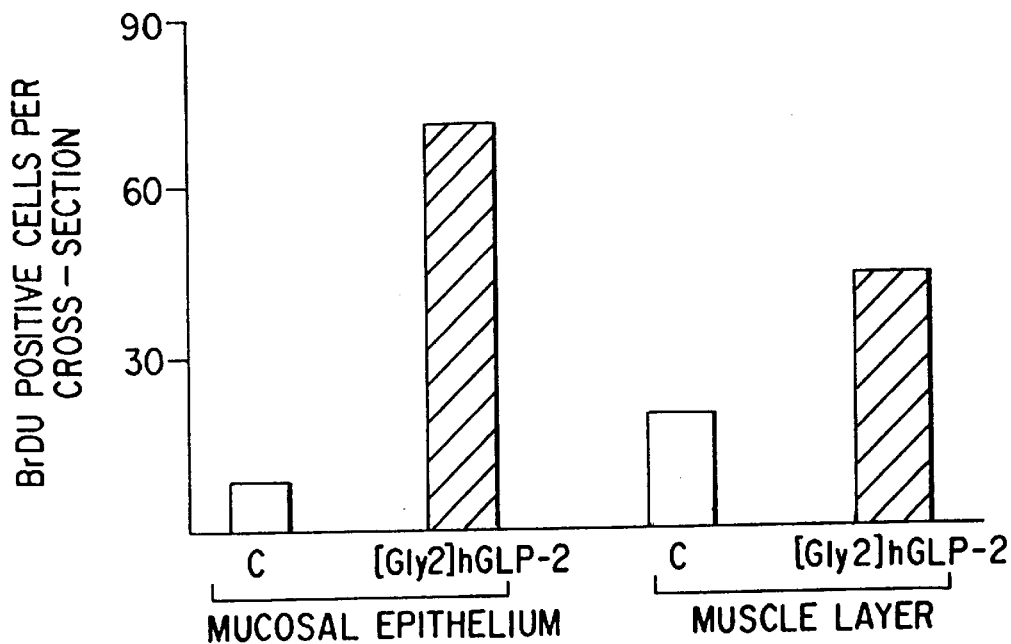
FIG. 1 illustrates the change in the number of cells which stain with bromodeoxyuridine, in the mucosal epithelium and muscle layer of the esophagus, after treatment with GLP-2.

The invention relates to therapeutic, prophylactic, and related uses of GLP-2 and GLP-2 analogs, in particular for the amelioration of medical or veterinary conditions in which functioning of the upper gastrointestinal tract is impaired by disease or injury. For example, the method is usefully applied to treat subjects suffering from an inflammatory condition involving the upper gastrointestinal tract, subjects who have undergone resection of the upper gastrointestinal tract, or subjects whose upper gastrointestinal tract has been damaged by toxins and the like.

As used herein the term "upper gastrointestinal tract" means that section of the gastrointestinal (GI) tract which comprises the esophagus and the stomach. The esophagus is that section of the GI tract that arises proximally at the pharyngoesophageal junction and continues distally through the posterior mediastinum to end at the gastroesophageal junction. The stomach is a distensible structure extending from the gastroesophageal junction to the duodenum.

As used herein the term "subject" includes a human or other mammal and including livestock and pets.

As used herein the term "GLP-2 receptor agonist" means any molecule which on binding to the GLP-2 receptor results in activation of the GLP-2 receptor, and includes for example GLP-2 or peptidic analogs of GLP-2. Recently it has been demonstrated that the GLP-2 receptor is a G-protein coupled receptor. Nucleic acid encoding the GLP-2 receptor has been isolated (see co-pending applications U.S. Ser. No. 08/767,224, filed Dec. 13, 1996, and U.S. Ser. No. 08/845,546, filed Apr. 24, 1997, both of which are incorporated herein by reference). Thus, methods commonly used in this field to identify G-protein coupled receptor agonists may be usefully applied to the GLP-2 receptor. One particularly useful methodology for assessing compounds for GLP-2 receptor agonist activity is disclosed in the above mentioned co-pending applications. Briefly, suitable cells such as COS cells are transformed with GLP-2 receptor encoding nucleic acid such that functional receptor is provided at the cell surface. Thereafter agonist activity of a test compounds can be assessed by contacting transformed cells by the test compound; an increase in the intracellular level of cyclic adenosine monophosphate in response to binding of the test compound to the transformed cells indicates agonist activity.

GLP-2 peptide analogs and selected chemical libraries, may be screened for GLP-2 receptor agonist activity using this approach. Guidance on the types of peptidic analogs that may be usefully employed in this method is given herein and in co-pending applications U.S. Ser. Nos. 08/632,533 and 08/631,273, both filed on Apr. 12, 1996, which are incorporated herein by reference. Moreover, any of the commercially available chemical libraries may be usefully screened for small molecule GLP-2 receptor agonists using high throughput or ultra high throughput screening technology. Peptidic analogs of GLP-2 and small molecule agonists identified as GLP-2 receptor agonists may be screened for therapeutic and related utility to treat conditions involving the upper gastrointestinal tract using the models described herein and in the scientific literature.

Any subject requiring enhancement of the activity of the upper gastrointestinal tract may potentially be a candidate for treatment with a GLP-2 agonist according to the invention. In particular, one group of conditions that may be beneficially treated according to the invention are diseases involving the esophagus. Human patients are typically diagnosed as having such a condition after manifesting one or more of the following symptoms: pain or discomfort on swallowing, pain or discomfort on swallowing liquids or solids, heartburn, a bitter taste in the mouth, a sensation of food sticking in the throat or during swallowing (often manifest as a lump in the throat) and shortness of breath. Visualization of the esophagus using esophagogastroscopy can be used to confirm the presence of damage or disease of the esophagus. Alternatively, the esophagus can be visualized radiologically using a barium contrast swallowing X-ray, or CT scan with an oral contrast material. The function of the esophagus can also be assessed by manometry. The presence of esophageal disease, particularly esophagitis, can be assessed functionally using the Bernstein test. For a more precise diagnosis of esophageal disease, biopsies can be taken of the esophageal mucosa for analysis of histological evidence of inflammation, and further, cultures can be made of this material to determine the presence of bacterial, viral or fungal infection and inflammation.

Inflammatory conditions of the esophagus include: inflammation-vasculitis, post-infection inflammation, infiltrative disorder, e.g., scleroderma and amyloid, as well as conditions wherein the inflammation results from the action of a toxin such as alcohol, acid, and alkali, such as from an accidental overdose.

Another group of conditions that may be beneficially treated, according to the invention, are diseases involving the stomach, e.g., peptidic ulcer. Human patients are typically diagnosed as having stomach disorders after manifesting symptoms of abdominal pain, either when at rest or with eating or both. However, symptoms of stomach disorder can be non-specific and it can be difficult to differentiate between pain from the esophagus and the stomach.

Additionally, GLP-2 may be beneficially administered to patients who can be demonstrated to be at risk of developing a malfunctioning of the upper gastrointestinal tract to protect against onset of the condition or reduce the severity of the attack. Such patients include smokers and patients with blood group O which is associated with duodenal ulcer and prepyloric ulcer, patients receiving or about to receive one or more NSAIDS, patients undergoing or about to undergo chemotherapy, and patients who suffer from stress-induced ulceration.

Treatment with GLP-2 agonists has been demonstrated to increase tissue growth in the upper gastrointestinal tract. Models suitable for determining which analogs of GLP-2 have upper gastrointestinal tract proliferation activity are potentially therapeutically useful to treat medical or veterinary conditions of the upper gastrointestinal tract are described in example 1 and example 3.

Animal models useful for studying conditions involving the esophagus are described in the literature (see, for example, *Ann. Surg. Oncol.* 1(3):252–261 (1994); *Ann. Emerg. Med.* 22(2):178–182 (1993)) and include mechanical injury or acid-induced injury of the esophagus. Thus, the animal models described in the art can be used to assess the ability of compounds identified as GLP-2 agonist to ameliorate inflammatory conditions involving the upper gastrointestinal tract.

Animal models useful for studying conditions involving the stomach are described in the literature (see, for example, *Experimental and Molecular Pathology* 59:136–154(1993)). These models include administration of non specific anti-inflammatories to cause gastroduodenitis, and administration of ethanol alone or in combination with other agents that cause gastric damage. Thus, the animal models described in the art can be used to assess the ability of compounds identified as GLP-2 agonist to ameliorate conditions involving the stomach.

The various vertebrate forms of GLP-2 include, for example, rat GLP-2 and its homologous including ox GLP-2, porcine GLP-2, degu GLP-2, bovine GLP-2, guinea pig GLP-2, hamster GLP-2, human GLP-2, rainbow trout GLP-2, and chicken GLP-2. The sequences of these forms of GLP-2 have been reported by many authors including Buhl et al. in *J. Biol. Chem.*, 1988, 263(18):8621, Nishi and Steiner, *Mol. Endocrinol.*, 1990, 4:1192–8, and Irwin and Wong, *Mol. Endocrinol.*, 1995, 9(3):267–77. The sequences reported by these authors are incorporated herein by reference.

Analogs of vertebrate GLP-2 can be generated using standard techniques of peptide chemistry and can be assessed for trophic activity at the upper gastrointestinal tract, all according to the guidance provided herein. Particularly preferred analogs of the invention are those based upon the sequence of human GLP-2, as follows:

His-Ala-Asp-Gly-Ser-Phe-Ser-Asp-Glu-Met-Asn-
Thr-Ile-Leu-Asp-Asn-Leu-Ala-Ala-Arg-Asp-Phe-
Ile-Asn-Trp-Leu-Ile-Gln-Thr-Lys-Ile-Thr-Asp wherein one or more amino acid residues are conservatively substituted for another amino acid residue, as long as the analog still maintains its trophic activity at the upper gastrointestinal tract as measured by an increase in at least one of the following parameters: upper gastrointestinal tract length, protein content, mass or rate of mitosis/cell division of cells of the upper gastrointestinal tract, measured, for example, by the use of an indirect indicator of mitosis such as bromodeoxyuridine(BrDU).

Conservative substitutions in any naturally occurring GLP-2, preferably the human GLP-2 sequence, are defined as exchanges within any of the following five groups:

I. Ala, Ser, Thr, Pro, Gly
II. Asn, Asp, Glu, Gln
III. His, Arg, Lys
IV. Met, Leu, Ile, Val, Cys
V. Phe, Tyr, Trp.

The invention also encompasses non-conservative substitutions of amino acids in any vertebrate GLP-2 sequence, provided that the non-conservative substitutions occur at amino acid positions known to vary in GLP-2 isolated from different species. Non-conserved residue positions are readily determined by aligning all known vertebrate GLP-2 sequences. For example, Buhl et al., *J. Biol. Chem.*, 1988, 263(18):8621, compared the sequences of human, porcine, rat, hamster, guinea pig, and bovine GLP-2's, and found that positions 13, 16, 19, 27 and 28 were non-conserved (position numbers refer to the analogous position in the human GLP-2 sequence). Nishi and Steiner, *Mol. Endocrinol.*, 1990, 4:1192–8, found that an additional position within the sequence encoding GLP-2, residue 20 in the above human sequence, also varied in degu, a rodent species indigenous to South America. Thus, under this standard, the amino acid positions which vary in mammals and which preferable may be substituted with non-conservative residues are positions 13, 16, 19, 20, 27 and 28. The additional amino acid residues which vary in vertebrates and which also may be substituted with non-conserved residues occur at positions 2, 5, 7, 8, 9, 10, 12, 17, 21, 22, 23, 24, 26, 29, 30, 31, 32 and 33.

Alternatively, non-conservative substitutions may be made at any position in which alanine-scanning mutagenesis reveals some tolerance for mutation in that substitution of an amino acid residue with alanine does not destroy all activity at the upper gastrointestinal tract. The technique of alanine scanning mutagenesis is described by Cunningham and Wells, *Science*, 1989, 244:1081, and incorporated herein by reference in its entirety. Since most GLP-2 sequences consist of only approximately 33 amino acids (and in human GLP-2 alanine already occurs at four positions), one of skill in the art could easily test an alanine analogue at each remaining position for effect, as taught in the examples below.

In specific embodiments of the invention, the GLP-2 peptide is selected from
1) rat GLP-2 having the sequence illustrated below:

His-Ala-Asp-Gly-Ser-Phe-Ser-Asp-Glu-Met-Asn-Thr-

Ile-Leu-Asp-Asn-Leu-Ala-Thr-Arg-Asp-Phe-Ile-Asn-

Trp-Leu-Ile-Gln-Thr-Lys-Ile-Thr-Asp;

2) human GLP-2, the $Thr^{19}$ to $Ala^{19}$ equivalent of rat GLP-2, illustrated below His-Ala-Asp-Gly-Ser-Phe-Ser-Asp-Glu-Met-Asn-Thr- Ile-Leu-Asp-Asn-Leu-Ala-Ala-Arg-Asp-Phe-Ile-Asn- Trp-Leu-Ile-Gln-Thr-Lys-Ile-Thr-Asp;

3) human [$Gly^2$]GLP-2 (human GLP-2 wherein the alanine at position 2 is replaced by a glycine);
4) GLP-2's, and GLP-2 analogs, which incorporate an N-terminal blocking group and/or an N-terminal extension such as Arg or Arg-Arg; and/or incorporate a C-terminal blocking group and/or a C-terminal extension such as Arg or Arg—Arg.

Further, a large number of agonist GLP-2 peptides that are described in PCT Application PCT/CA97/00252, filed Apr.

11, 1997, incorporated in its entirety by reference herein, may also be used in the methods of the invention.

The "blocking groups" represented by R1 and R2 are chemical groups that are routinely used in the art of peptide chemistry to confer biochemical stability and resistance to digestion by exopeptidase. Suitable N-terminal protecting groups include, for example, $C_{1-5}$alkanoyl groups such as acetyl. Also suitable as N-terminal protecting groups are amino acid analogues lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$ alkyl groups, e.g., methyl, ethyl, and propyl groups, while amide-forming groups include amino functions such as primary amine, or alkylamine functions, e.g., mono-$C_{1-5}$alkylamino and di-$C_{1-5}$alkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine.

The particular form of GLP-2 selected for promoting the growth of upper gastrointestinal tract tissue can be prepared by a variety of techniques well known for generating peptide products. Vertebrate forms of GLP-2 can of course be obtained by extraction from the natural source, using an appropriate combination of protein isolation techniques. As described by Buhl et al., supra, porcine GLP-2 isolation and purification is achieved from acid-ethanol extracts of ileal mucosa by a combination of size selection and HPLC-based fractionation, with the aid of antibody raised against synthetic proglucagon 126–159, to monitor work-up. As an alternative to GLP-2 extraction, those forms of GLP-2 that incorporate only L-amino acids, whether vertebrate GLP-2 or analogs thereof, can be produced in commercial quantities by application of recombinant DNA technology. For this purpose, DNA coding for the desired GLP-2 or GLP-2 analog is incorporated into an expression vector and transformed into a microbial, e.g., yeast, or other cellular host, which is then cultured under conditions appropriate for GLP-2 expression. A variety of gene expression systems have been adapted for this purpose, and typically drive expression of the desired gene from expression controls used naturally by the chosen host. Because GLP-2 does not require post translational glycosylation for its activity, its production may most conveniently be achieved in bacterial hosts such as *E. coli*. For such production, DNA coding for the selected GLP-2 peptide may usefully be placed under expression controls of the lac, trp or PL genes of *E. coli*. As an alternative to expression of DNA coding for the GLP-2 per se, the host can be adapted to express GLP-2 peptide as a fusion protein in which the GLP-2 is linked releasable to a carrier protein that facilitates isolation and stability of the expression product.

In an approach universally applicable to the production of a selected GLP-2 or GLP-2 analog, and one used necessarily to produce GLP-2 peptides that incorporate non-genetically encoded amino acids and N- and C-terminally derivatized forms, the well established techniques of automated peptide synthesis are employed, general descriptions of which appear, for example, in J. M. Stewart and J. D. Young, *Solid Phase Peptide Synthesis,* 2nd Edition, 1984 Pierce Chemical Company, Rockford, Ill.; and in M. Bodanszky and A. Bodanszky, *The Practice of Peptide Synthesis,* 1984, Springer-Verlag, N.Y.; Applied Biosystems 430A Users Manual, 1987, ABI Inc. Foster City, Calif. In these techniques, GLP-2 peptide is grown from its C-terminal, resin-conjugated residue by the sequential addition of appropriately protected amino acids, using either the Fmoc or tboc protocols, as described for instance by Orskov et al., *Febs Letters,* 1989, 247(2):193–196.

For the incorporation of N- and/or C-blocking groups, protocols conventional to solid phase peptide synthesis methods can also be applied. For incorporation of C-terminal blocking groups, for example, synthesis of the desired peptide is typically performed using, as solid phase, a supporting resin that has been chemically modified so that cleavage from the resin results in a GLP-2 peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally aminated peptide. Similarly, incorporation of an N-methylamine blocking group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxybenzyl alcohol or equivalent linker, can be used for this purpose, with cleavage from the support being effected by TFA in dichloromethane. Esterification of the suitably activated carboxyl function, e.g., with DCC, can then proceed by addition of the desired alcohol, followed by deprotection and isolation of the esterified GLP-2 peptide.

Incorporation of N-terminal blocking groups can be achieved while the synthesized GLP-2 peptide is still attached to the resin, for instance by treatment with suitable anhydride and nitrile. To incorporate an acetyl blocking group at the N-terminus, for instance, the resin-coupled peptide can be treated with 20% acetic anhydride in acetonitrile. The N-blocked GLP-2 peptide can then be cleaved from the resin, deprotected and subsequently isolated.

Once the desired GLP-2 peptide has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g., $C_4$-, $C_8$-, or $C_{18}$-silica. Such column fractionation is generally accomplished by running linear gradients, e.g., 10–90%, of increasing % organic solvent, e.g., acetonitrile, in aqueous buffer, usually containing a small amount (e.g., 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the GLP-2 peptide is then treated in the established manner to exchange the cleavage acid (e.g., TFA) with a pharmaceutically acceptable acid, such as acetic, hydrochloric, phosphoric, maleic, tartaric, succinic and the like, to generate a pharmaceutically acceptable acid addition salt of the peptide.

For administration to patients, the GLP-2 peptide or its salt is provided, in one aspect of the invention, in pharmaceutically acceptable form, e.g., as a preparation that is sterile-filtered, e.g., through a 0.22μ filter, and substantially pyrogen-free. Desirably, the GLP-2 peptide to be formulated migrates as a single or individualized peak on HPLC, exhibits uniform and authentic amino acid composition and sequence upon analysis thereof, and otherwise meets standards set by the various national bodies which regulate quality of pharmaceutical products.

For therapeutic use, the chosen GLP-2 or GLP-2 analog is formulated with a carrier that is pharmaceutically acceptable and is appropriate for administering the peptide to the subject by the chosen route of administration so as to deliver the peptide to the upper gastrointestinal tract. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, e.g., when used as liquid nutritional supplements for patients on total parenteral nutrition therapy, or by injection, e.g., sub-cutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of the GLP-2 or GLP-2 analog may be enhanced, if desired, by incorporating a solubility enhancer, such as acetic acid or sodium hydroxide.

The aqueous carrier or vehicle can be supplemented for use as injectables with an amount of gelatin effective to achieve the depot effect are expected to lie in the range from 10–20%. Alternative gelling agents, such as hyaluronic acid, may also be useful as depoting agents (also veterinary applications).

As an alternative to injectable formulations, the GLP-2 or GLP-2 analog may be formulated for administration to patients and delivery to the upper gastrointestinal tract by other routes. Oral dosage forms, such as tablets, capsules and the like, can be formulated in accordance with standard pharmaceutical practice.

The compounds may also be formulated in liquid form to provide direct contact with the esophagus and stomach, in lozenge form or other similar formulations which permit direct contact with the lining of the esophagus or stomach and the compound. Further, standard formulations may be delivered to achieve rapid and high levels of the compound in the circulation.

The GLP-2's and GLP-2 analogs of the invention may also be formulated as a slow release implantation device for extended and sustained administration of GLP-2. Examples of such sustained release formulations include composites of bio-compatible polymers, such as poly(lactic acid), poly (lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems", Vol. 45 of "Drugs and the Pharmaceutical Sciences", M. Dekker, New York, 1990. Liposomes may also be used to provide for the sustained release of a GLP-2 or GLP-2 analog. Details concerning how to use and make liposomal formulations of drugs of interest can be found in, among other places, U.S. Pat. No. 4,921,706; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat No. 4,725,442; U.S. Pat. No. 4,737,323; U.S. Pat. No. 4,920,016. Sustained release formulations are of particular interest when it is desirable to provide a high local concentration of a GLP-2 or GLP-2 analog, e.g., near or at the upper gastrointestinal tract to promote upper gastrointestinal tract growth in the inflamed upper gastrointestinal tract.

For use in stimulating growth of the upper gastrointestinal tract, and/or enhancing upper gastrointestinal tract functioning in a mammal including a human, the present invention provides in one of its aspects a package, in the form of a sterile-filled vial or ampoule, that contains a tissue growth promoting amount of the GLP-2 or GLP-2 analog, in either unit dose or multi-dose amounts, wherein the package incorporates a label instructing use of its contents for the promotion of such growth. In one embodiment of the invention, the package contains the GLP-2 or GLP-2 analog and the desired carrier, as an administration-ready formulation. Alternatively, and according to another embodiment of the invention, the package provides the GLP-2 or GLP-2 analog in a form, such as a lyophilized form, suitable for reconstitution in a suitable carrier, such as phosphate-buffered saline.

In one embodiment, the package is a sterile-filled vial or ampoule containing an injectable solution which comprises an effective, upper gastrointestinal tract proliferating amount of GLP-2 or GLP-2 analog dissolved in an aqueous vehicle.

According to the present invention, the GLP-2 or GLP-2 analog is administered to treat patients that would benefit from growth of the tissue of the upper gastrointestinal tract. In addition, patients who would benefit from increased upper gastrointestinal tract tissue function, whether as a result of increased tissue growth or not, are candidates for treatment with the invention. In general, patients who would benefit from either increased upper gastrointestinal tract mass and/or increased upper gastrointestinal tract mucosal function are candidates for treatment with GLP-2 or GLP-2 analog. Particular conditions that may be treated with GLP-2 include the various forms of inflammatory diseases of the stomach or esophagus, as well as patients who have undergone partial or sub-total resection of the upper gastrointestinal tract. For convenience a non-exhaustive list of conditions of the upper gastrointestinal tract including the stomach and esophagus, that may be treated by the subject GLP-2 or in combinations, is provided in the following tables.

TABLE 1

Disorders of the Stomach

I. Acute Gastritis
   A. Acute hemorrhagic and erosive gastritis
      1. Acute erosive gastritis
      2. Acute hemorrhagic gastritis
      3. Acute gastritis
      4. Acute stress gastritis
      5. Nonsteroidal anti-inflammatory drug
      6. Gastropathy (acute)
      7. Hemorrhagic gastropathy TABLE 1-continued Disorders of the Stomach

- B. Acute *Helicobacter pylori* gastritis
    1. Type B gastritis
    2. Hypersecretory gastritis
    3. Non specific gastritis secondary to *Helicobacter pylori*
    4. *Helicobacter pylori* - associated gastritis
- C. Chemical gastritis
    1. Type C gastritis (i.e., chemical)
    2. Reactive gastritis
    3. Reflux gastritis
    4. Bile gastritis
    5. Nonsteroidal anti-inflammatory drug gastropathy (chronic)
- D. Other acute infectious gastritis (See Uncommon Forms of Gastritits)

II. Common Forms of Chronic Gastritis
- A. *Helicobactor pylori* gastritis
- B. Chemical gastritis
    1. Bile reflux
    2. Type C gastritis (i.e., chemical)
    3. Reactive gasttitis
    4. Reflux gastritis
    5. Aspirin and nonsteroidal anti-inflammatory drug gastropathy (chronic)
- C. Metaplastic atrophic gastritis
    1. Autoimmune Metaplastic atrophic gastritis
        a. Atrophic gastritis
        b. Type A gastritis
        c. Diffuse corporal gastritis
        d. Autoimmune chronic gastritis
        e. Autoimmune-associated gastritis
    2. Environmental metaplastic atrophic gastritis
        a. Environmental chronic gastritis
        b. Multifocal environmental gastritis
        c. Multifocal atrophic gastritis
        d. Atrophic gastritis
        e. Chronic atrophic gastritis
        f. Type B gastritis
        g. Idiopathic pangastritis III. Uncommon Forms of gastritis
- A. Postantrectomy atrophic gastritis
- B. Eosinophilic gastritis
- C. Infectious gastritis
    1. Bacterial (other than *Helicobacter pylori*)
        a. *Gastrospirillum hominis*
        b. Phlegmonous
        c. Mycobacterial
        d. Syphiltic
    2. Viral
    3. Parasitic
    4. Fungal
- D. Crohn's disease
- E. Sarcoidosis
- F. Isolated granulomatous gastritis
- G. Lymphocylic gastritis
- H. Ménétriere's disease See, *Gastritis, Doudenitis, and Associated Ulcerative Lesions*, by John H. Yardley and Thomas R. Hendrix, in Textbook on Gastronenterology Vol. I, edited by Tadataka Yamada M. D. (2nd ed. 1985).

TABLE 2

Disorders of the Esophagus

I. Infectious Esophagitis
- A. Organisms associated with infections
    1. Fungi
        a. Candida species (esp. albicans)
        b. Aspargillus species TABLE 2-continued Disorders of the Esophagus c. *Histoplasma capsulatum*
        d. *Blastomyces dermatitides*
    2. Viruses
        a. Herpes simplex virus (type 1)
        b. Cytomegalovirus
        c. Varicella-zoster virus
    3. Bacteria
        a. *Mycobacterium tuberculosis*
        b. *Actinomyces Israelii*
        c. *Streptococcus viridans*
        d. *Lactobacillus acidophilus*
        e. *Treponema pallidum*

II. Non-infectious Esophagitis
III. Acid Reflux
IV. Bile Reflux
V. Chemical Injury
- A. Medicines
- B. Toxins
- C. Acids
- D. Alkali VI. Sarcoidosis
VII. Crohn's disease
VIII. Behcet's disease
IX. Graft-versus-host disease
X. AIDS Related Infections
- A. Cryptosporidium sp
    Microsporidium sp
    *Isospora beill*
    Glardia Lamblia
    Salmonella sp
    Shigella sp
    Campylobacter sp
    Mycobacterium tuberculosis
    *Mycobacterium avium* complex (MAC)
    *Clostridium difficile*
    Cytomeglavorius
    Herpes simplex See, *Miscellaneous Diseases of the Esophagus*, in in Textbook on Gastronenterology Vol. I, edited by Tadataka Yamada M. D. (2nd ed. 1985).

The therapeutic efficacy of the GLP-2 treatment on the esophagus may be monitored by, for example, endoscopy, barium swallow or CT. For example, GLP-2 or GLP-2 analog is administered to a patient with an inflammatory condition involving the upper gastrointestinal tract in an amount sufficient to ameliorate the esophageal discomfort, decrease pain, improve swallowing, reduce chest pain, decrease heartburn, decrease regurgitation of solids or liquids after swallowing or eating, decrease in vomiting, or improve weight gain or improve vitality. The therapeutic efficacy of GLP-2 on the stomach amy be monitored by a decrease in pain or discomfort. Additionally, GLP-2 or GLP-2 analog may be administered to patients who are identified as being at risk of developing an inflammatory condition involving the upper gastrointestinal tract such as patients treated with nonsteroidal anti-inflammatories ("NSAIDS"). A few examples of NSAIDS are aspirin, ibuprofen, sulindac, and indomethocin.

The therapeutic dosing and regimen most appropriate for patient treatment will of course vary with the disease or condition to be treated, and according to the patient's weight and other parameters. The results presented hereinbelow in Examples 1–3 demonstrate that treatment with GLP-2 or GLP-2 analog administered twice daily over 2 days results in cell proliferation increase in protein synthesis of the upper gastrointestinal tract. Treatment for 12 days resulted in an increase in stomach mass. Example 4 demonstrates that GLP-2 treatment is able to ameliorate the gastrointestinal toxicity of nonsteroidal anti-inflammatory drugs. It is expected that much smaller doses, and shorter or longer duration or frequency of treatment, will also produce therapeutically useful results, i.e., a statistically significant increase particularly in upper gastrointestinal tract mass, and/or enhanced upper gastrointestinal tract functioning. The dosage sizes and dosing regimen most appropriate for human use are guided by the results herein presented, and can be confirmed in properly designed clinical trials.

An effective dosage and treatment protocol may be determined by conventional means, starting with a low dose in laboratory animals and then increasing the dosage while monitoring the effects, (e.g., histology, disease activity scores, mucosal enzyme activity, small and large bowel epithelial-specific gene expression, markers of the inflammatory response such as expression of cytokines and myeloperoxidase, GLP-2 content) and systematically varying the dosage regimen as well. Numerous factors may be taken into consideration by a clinician when determining an optimal dosage for a given subject. Primary among these is the amount of GLP-2 normally circulating in the plasma, which is on the order of 151 pmol/mL in the resting state, rising to 225 pmol/mL after nutrient ingestion for healthy adult humans (Orskov, C. and Holst, J. J., 1987, *Scand. J. Clin. Lab. Invest.* 47:165). Additional factors include the size of the patient, the age of the patient, the general condition of the patient, the particular disease being treated, the severity of the disease, the presence of other drugs in the patient, the in vivo activity of the GLP-2 peptide and the like. The trial dosages would be chosen after consideration of the results of animal studies and the clinical literature. It will be appreciated by the person of ordinary skill in the art that information such as binding constants and Ki derived from in vitro GLP-2 binding competition assays may also be used in calculating dosages.

A typical human dose of a GLP-2 peptide would be from about 10 µg/kg body weight/day to about 10 mg/kg/day, preferably from about 50 µg/kg/day to about 5 mg/kg/day, and most preferably about 100 µg/kg/day to 1 mg/kg/day.

In another of its aspects, the invention provides for the treatment of patient candidates as just identified using implanted cells that have either been conditioned in vitro or in vivo by prior incubation or treatment with GLP-2 or GLP-2 analog, or have been engineered genetically to produce it. Conditioning of the cells ex vivo can be achieved simply by growing the cells or tissue to be transplanted in a medium that has been supplemented with a growth-promoting amount of the GLP-2 or GLP-2 analog and is otherwise appropriate for culturing of those cells. The cells can, after an appropriate conditioning period, then be implanted either directly into the patient or can be encapsulated using established cell encapsulation technology, and then implanted.

Yet another aspect of the invention encompasses treating animals in vivo with GLP-2 peptides in order to promote the growth of esophageal tissue. After subsequent enlargement of the upper gastrointestinal tract these tissues may then be used in a xenotransplantation procedure. Such GLP-2 peptide treatment can be advantageous prior to xenotransplantation of the tissue from a non-human animal to a human because the size of the transplanted organ or tissue often limits the success of this procedure. For example, a porcine donor animal may be treated with GLP-2 peptide in order to increase upper gastrointestinal tract size prior to xenotransplantation of the porcine upper gastrointestinal tract tissue into a human in need of this organ.

Alternatively, the cells to be implanted can be raised in vitro from a cell that has been engineered genetically to express or to over-express either the glucagon gene or, more directly, DNA coding solely for GLP-2. The sequence of such DNA can readily be determined from the amino acid sequence of the selected GLP-2, with the limitation that only GLP-2 forms containing genetically encoded amino acids can be produced in this manner. Various viral vectors, suitable for introduction of genetic information into human cells, can be employed and will incorporate the GLP-2-encoding DNA under expression controls functional in the host cells. Once altered genetically, the engineered cells can then be implanted using procedures established in the art. (See, for example, Drucker et al., 1996, PNAS:USA 93:7911–7916.)

Coadministration of GLP-2 and Other Peptide Hormones

The invention relates to therapeutically useful combinations of GLP-2 and at least one other peptide hormone selected from the group consisting of IGF-1, IGF-2, and GH. Surprisingly, GLP-2 (and its analogs) administered alone to a mammal induces the growth of the upper gastrointestinal tract. As predicted, when GLP-2 is administered in combination with at least one other peptide hormone selected from the group IGF-1, IGF-2, and GH, there are clear effects on the growth of upper gastrointestinal tract tissue are seen.

The GLP-2's and GLP-2 analogs of the invention may also be administered to a subject in admixture with at least one other peptide hormone which is known to be an esophageal or gastric growth factor. Known esophageal and gastric growth factors include epidermal growth factor (EGF), insulin-like growth factor 1 (IGF-1), hepatocyte growth factor (HGF) and keratinocyte growth factor (KGF).

Specific adjunct therapies with GLP-2 useful for the treatment of conditions involving the stomach, e.g., peptidic ulcer include: (1) agents that act to block acid secretion from the stomach, e.g., H2 receptor antagonists, proton pump inhibitors and prostaglandins; (2) agents that act to form a protective barrier in the stomach, e.g., sucralfate; (3) bismuth containing compounds, and (4) agents that control *Helicobacter pylori*.

More particularly, the invention relates to the therapeutic and related uses of GLP-2 when co-administered with at least one other peptide hormone selected from the group consisting of IGF-1 and GH. Even more particularly, the invention relates to the uses of the above-mentioned combinations to enhance upper gastrointestinal tract functioning. Most particularly, the invention relates to the therapeutic and related uses of the above-mentioned combinations to promote the proliferation of the mucosal epithelial and muscle cells of the upper gastrointestinal tract.

Unless otherwise specified, the term "GLP-2" refers collectively herein to the various naturally produced forms of GLP-2, particularly mammalian forms. The invention also encompasses those analogs of GLP-2 which exhibit activity. Analogs of GLP-2 can be tested for activity using the mouse model described herein and in co-pending application U.S. Ser. No. 08/631,273. Briefly, this testing involves a 10 to 14 day regimen of twice a day (b.i.d) subcutaneous injection of 2.5 mg of the GLP-2 analog (in PBS) per kg body weight with control matched untreated animals receiving PBS alone. Alternatively, the analogs may be administered once a day, or every other day. Upon completion of the regimen the animals are sacrificed and their upper gastrointestinal tracts are removed and weighed. In this manner, the effect of analogs of GLP-2 on the upper gastrointestinal tract can be assessed.

Guidance on particular analogs and variants of GLP-2 that may be usefully employed in the present invention, and guidance on how to produce others, is provided in co-pending applications U.S. Ser. Nos. 08/632,533 and 08/631,273, both filed on Apr. 12, 1996, the disclosures of which are incorporated herein by reference. Briefly, any substitution, addition or deletion of GLP-2 that does not destroy the activity of GLP-2 may be usefully employed in this invention. In preferred embodiments the GLP-2 analogs are at least as as native human GLP-2. In the most preferred embodiments, the GLP-2 analog has enhanced activity compared with native human GLP-2. For example, such analogs may exhibit enhanced serum stability, enhanced receptor binding and enhanced signal transducing activity. Other modifications to GLP-2 and GLP-2 analogs that may usefully be employed in this invention are those which render the molecule resistant to oxidation.

The GLP-2 analogs are suitably analogs of either human GLP-2 (human [Gly$^2$] GLP-2) or rat GLP-2 (rGLP-2). In a preferred embodiment of the invention, rat or human GLP-2 is altered at position 2 to confer DPP-IV resistance by substituting a Gly for an Ala. Human GLP-2 having Gly substituted for Ala at position 2 is referenced herein as [Gly 2] human [Gly$^2$] GLP-2.

Similarly, the terms "IGF-1", "IGF-2" and "GH" as used herein encompass effective analogs and variants of the naturally produced peptides as well as the native peptides. Guidance on particular analogs and variants of IGF-1, IGF-2, and GH that may usefully be employed in the present invention is provided in the following publications which are incorporated herein by reference: Vanderhoof et al. (1992) *Gastroenterology* 102:1949–1956; Steeb et al. (1994) *Am. J. Physiol.* 266:G1090–G1098; and Jones et al. (1995) *Endocrine Reviews* 16:3–34; Conlon et al. (1995) *Journal of Endocrinology* 146:247–253; Francis et al. (1993) *Biochemical Journal* 293:713–719; Lewis et al., WO 93/20836; and Bozyczko-Coyne et al., WO 93/08826.

Secretagogues, factors capable of enhancing endogenous production, of the subject peptide hormones may also be included as part of a therapeutic regimen, either in lieu of or as a supplement to the subject peptide hormone the release of which it stimulates. Thus, the inclusion of such factors, which are well known to those of ordinary skill in the art, is within the scope of the invention. For example, production of endogenous GH is increased by growth hormone releasing factor (GHRF) and by arginine. Similarly, the skilled artisan will be aware that compounds such as small molecules, which act on the appropriate receptor to cause an increase in the serum levels of any of the subject peptide hormone, could be usefully employed in the present invention.

As used herein, a compound, such as a peptide, is said to be "co-administered" or in "combination" with another compound when either the physiological effects of both compounds, or the elevated serum concentration of both compounds can be measured simultaneously. With compounds that increase the level of endogenous production, the serum concentration of the endogenously produced hormone and the other administered agent can also be measured simultaneously when "co-administered" or in "combination". Thus, compounds may be administered either simultaneously, as separate or mixed compositions, or they may be administered sequentially provided that a constant elevation of their levels in serum results.

Unless otherwise stated the terms "combination therapy" and "combination treatments" are used herein to describe a therapeutic regimen involving co-administration of the subject peptide hormones which results in an enhancement of the nutritional status, or an increase in intestinal mass, of a patient.

As used herein, the terms "enhanced nutritional status" and "enhanced gut functioning" are defined as any increase in bodily uptake of nutrients over pretreatment levels. Such nutrients include, but are not limited to, carbohydrates, protein and amino acids, fat, cholesterol and fat-soluble vitamins, water soluble vitamins, and minerals. Minerals, the uptake of which can be increased by the methods of the present invention, include, but are not limited to, Na, Ca, Mg, K, Zn, and Fe. Vitamins, the absorption of which can be increased by the present invention include fat soluble vitamins such as vitamins A, D, E and K as well as water soluble vitamins such as B$^{12}$ and folic acid.

As used herein the term "patient" is intended to include, but is not limited to humans, livestock and pets.

A mammal is said to be suffering from disorders, diseases and medical conditions of the gut when the absorptive properties of the gut of the mammal are diminished, and/or when inflammation or injury to the gastrointestinal tract is present so as to cause discomfort and illness. A variety of tests can be employed to determine if a mammal is suffering from malabsorption syndrome. These include stool fat content, xylose absorption, gastrointestinal x-ray studies, small intestine biopsy test, the Schilling test for vitamin B$^{12}$ absorption and the secretin test.

In one aspect of the invention, GLP-2 is provided for administration to patients in admixture with at least one other peptide hormone selected from the group consisting of IGF-1, IGF-2, and GH in pharmaceutically acceptable form (for example, as a preparation that is sterile filtered through a 0.22 $\mu$m filter and substantially pyrogen free). Desirably, the peptides to be admixed migrate as single peaks on HPLC.

The particular forms of GLP-2, IGF-1, IGF-2 and GH selected for the invention can be prepared by a variety of techniques well known for generating peptide products. Those forms of GLP-2, IGF-1, IGF-2 and GH that occur naturally can of course be obtained by extraction from the natural source, using an appropriate combination of protein isolation techniques. For example, as described by Buhl et al., (1988) *J. Bio. Chem.* 263(18):8621–8624, porcine GLP-2 isolation and purification is achieved from acid-ethanol extracts of ileal mucosa by a combination of size selection and HPLC-based fractionation, with the aid of antibody raised against synthetic proglucagon 126–159, to monitor work-up. Similarly, GH can be extracted from cadavers as described in U.S. Pat. No. 2,974,088.

As an alternative to extraction, those forms of GLP-2, IGF-1, IGF-2 and GH that incorporate only L-amino acids can be produced reproducibly and in commercial quantities by application of recombinant DNA technology. For this purpose, nucleic acids coding for the desired form of GLP-2, IGF-1 (see, for example, U.S. Pat. No. 5,288,931), IGF-2 and GH (see, for example, Goeddel et al. (1979) *Nature* 281:544–548) are incorporated expressibly in a cellular host, which is then cultured under conditions appropriate for expression of that particular peptide or protein. A variety of gene expression systems have been adapted for this purpose, and typically drive expression of the desired gene from expression controls used naturally by the chosen host. Because GLP-2, IGF-1, IGF-2 and GH do not require post translational modification for activity, their production may conveniently be achieved in bacterial hosts such as *E. coli*. For such production, DNA coding for the selected GLP-2, IGF-1, IGF-2 or GH may usefully be placed under expression controls of the lac, trp or PL genes of *E. coli*. As an alternative to expression of DNA coding for the GLP-2, IGF-1, IGF-2 or GH per se, the host can be adapted to express GLP-2, IGF-1, IGF-2 or GH as a fusion protein in which the GLP-2, IGF-1, IGF-2 or GH is linked releasably to a carrier protein that facilitates isolation and stability of the expression product.

For therapeutic use, the peptide hormones chosen for use in combination therapy are formulated with at least one carrier that is pharmaceutically acceptable and is appropriate for delivering the peptides by the chosen route of administration. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion or by injection, either sub-cutaneously or intravenously, and are accordingly utilized as aqueous solutions in sterile and pyrogen-free form and optionally buffered to a slightly acidic or physiological pH. Thus, the compounds may be administered in distilled water or, more desirably, in saline, buffered saline or 5% dextrose solution. Water solubility of these compounds may be enhanced, if desired, by incorporating a solubility enhancer, such as the inclusion of acetic acid for GLP-2 formulations.

The subject invention also provides for various peptide hormone conjugates. The peptide hormone compositions of the invention comprise peptide hormone covalently linked to one or more water soluble polymers. Water soluble polymers, especially polyethylene glycol, have been conjugated to proteins so as to provide additional desirable properties while retaining, at least in part, the growth inducing properties of the peptide hormone. These desirable properties include increased solubility in aqueous solutions, increased stability in storage, reduced immunogenicity, increased resistance to proteolytic degradation, and increased in vivo half-life. Water soluble polymers suitable for use in the subject compositions include polyethylene glycol homopolymers, polypropylene glycol homopolymers, copolymers of ethylene glycol with propylene glycol, wherein said homopolymers and copolymers are unsubstituted or substituted at one end with an alkyl group, polyoxethylated polyols, polyvinyl alcohol, polysaccharides, polyvinyl ethyl ethers, and $\alpha,\beta$-poly[(2-hydroxyethyl)-DL-aspartamide]. Polyethylene glycol is particularly preferred. Methods of making water-soluble polymer conjugates of proteins are described in, among other places, U.S. Pat. No. 4,179,337; U.S. Pat. No. 4,609,546; U.S. Pat. No. 4,261,973; U.S. Pat. No. 4,055,635; U.S. Pat. No. 3,960,830; U.S. Pat. No. 4,415,665; U.S. Pat. No. 4,412,989; U.S. Pat. No. 4,002,531; U.S. Pat. No. 4,414,147; U.S. Pat. No. 3,788,948; U.S. Pat. No. 4,732,863; U.S. Pat. No. 4,745,180; EP No. 152,847; EP No. 98,110 (published Jan. 11, 1984); JP No. 5,792,435.

Another aspect of the invention is formulations that provide for the sustained release of peptide hormones. Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al. (1992) *Polymers for Advanced Technologies* 3:279–292. Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical Sciences," M. Dekker, New York, 1990.

Liposomes may also be used to provide for the sustained release of peptide hormones. Details concerning how to use and make liposomal formulations of drugs of interest can be found in, among other places, U.S. Pat. No 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of the compositions of the invention, e.g., near or in the upper gastrointestinal tract.

For use in stimulating upper gastrointestinal growth and/or improving upper gastrointestinal tissue function in a mammal including a human, the present invention provides in one of its aspects a package, in the form of a sterile-filled vial or ampoule, that contains a tissue growth promoting amount of GLP-2 in admixture with at least one other peptide hormone selected from the group consisting of IGF-1, IGF-2 and GH in either unit dose or multi-dose amounts, wherein the package incorporates a label instructing use of its contents for the promotion of gastrointestinal functioning, e.g., for promotion of growth of the upper gastrointestinal tract. In one embodiment of the invention, the package contains GLP-2 and at least one other peptide hormone selected from the group consisting of IGF-1, IGF-2 and GH, and the desired carrier, as an administration-ready formulation. Alternatively, and according to another embodiment of the invention, the package provides the GLP-2 and at least one other peptide hormone selected from the group consisting of IGF-1, IGF-2 and GH in a form, such as a lyophilized form, suitable for reconstitution in a suitable carrier, such as buffered saline. In yet another embodiment, the package is a sterile-filled vial or ampoule containing an injectable solution which comprises an effective amount of GLP-2 and at least one other peptide hormone selected from the group consisting of IGF-1, IGF-2 and GH dissolved in an aqueous vehicle.

According to the present invention, the GLP-2 in combination with at least one other peptide hormone selected from the group consisting of IGF-1, IGF-2 and GH is administered to treat patients who would benefit from enhanced upper gastrointestinal tract functioning. In one aspect, patient candidates are those who would benefit from proliferation of the upper gastrointestinal tract tissue. In addition, patient candidates are those who would benefit from increased upper gastrointestinal tract tissue function, whether as a result of increased tissue growth or not. The effects of combination therapy on these tissues, would clearly benefit those patients suffering from diseases or conditions marked by abnormalities. In general, patients who would benefit from increased upper gastrointestinal tract mass or regeneration and healing of preexistent normal mucosal epithelium are candidates for treatment with the invention. In addition, patients who would benefit from increased upper gastrointestinal tract tissue function, whether as a result of increased tissue growth or not, are candidates for treatment with the invention. For example, patients may be treated prior to or after a regimen of chemotherapy or radiotherapy, prior to, during, or following the onset of gastrointestinal inflammation, after a period of parenteral nutrition, after or during active gastrointestinal disease, or if the patient is a premature infant with insufficient maturation of the gastrointestinal tract, and/or inflammation of the GI tract as exemplified by the condition necrotizing enterocolitis.

Numerous factors may be taken into consideration by a clinician when determining an optimal dosage for a given subject. Primary among these is the amount of peptide hormone normally produced by the body. Additional factors include the size of the patient, the age of the patient, the general condition of the patient, the particular disease being treated, the severity of the disease, the presence of other drugs in the patient, the in vivo activity of the peptide or peptide analog and the like. The trial dosages would be chosen after consideration of the results of animal studies and the clinical literature with respect to administration of peptide hormones and peptide hormone secretagogues. It will be appreciated by the person of ordinary skill in the art that information such as binding constants and Ki derived from in vitro binding competition assays may also be used in calculating dosages. It is expected that doses of the combination equivalent to about 0.1 mg/kg of GLP-2 and GLP-2 analogs twice daily, with approximately 2 mg/kg of IGF-1 twice daily and/or 1 mg/kg of GH once a day, co-administered over 10 days can generate very significant increases in the upper gastrointestinal tract. It is expected that much smaller doses, in the $\mu$g/kg range and perhaps into the ng/kg range, and perhaps shorter or longer duration or frequency of treatment, will also produce therapeutically useful results, e.g., a statistically significant increase, particularly in small intestine mass.

A typical human dose of a GLP-2 peptide would be from about 10 $\mu$g/kg body weight/day to about 10 mg/kg/day, preferably from about 50 $\mu$g/kg/day to about 5 mg/kg/day, and most preferably about 100 $\mu$g/kg/day to 1 mg/kg/day. As the GLP-2 analogs of the invention can be up to 10 to even 100 times more potent than GLP-2, a typical dose of such a GLP-2 analog may be lower, for example, from about 100 ng/kg body weight/day to 1 mg/kg/day, preferably 1 $\mu$g/kg/day to 500 $\mu$g/kg/day, and even more preferably 1 $\mu$g/kg/day to 100 $\mu$g/kg/day.

For administration of GH to a mammal, particularly humans, a dose range of 0.02–2.5 mg/kg/day may be used; preferably, GH doses may range from about 0.1–2 mg/kg/day. For administration of IGF's, dosages may be in the range of 1 $\mu$g to 1 g/kg/day. IGF-1 is preferably administered to humans in the range of about 0.03–10 mg/kg/day, more preferably from about 0.1–4 mg/kg/day, and most preferably from around 0.5–1 mg/kg/day. Typical doses for IGF-2 are about 0.5–5 mg/kg/day. The dose required for analogues of IGF may be 20–50% less than naturally occurring IGF-1. Further, the dosage sizes and dosing regimen most appropriate for human use can be determined in properly designed clinical trials.

In another of its aspects, the invention provides for the treatment of patients as just identified using implanted intestinal cells that have been regenerated or stimulated to proliferate in vitro or in vivo prior to reimplantation or transplantation into a recipient. Conditioning of the cells ex vivo can be achieved simply by growing the cells or tissue to be transplanted in a medium that has been supplemented with a growth-promoting amount of the combinations and is otherwise appropriate for culturing of those cells. The cells can, after an appropriate conditioning period, then be implanted either directly into the patient or can be encapsulated using established cell encapsulation technology, and then implanted. Analogous procedures with other organs, such as the skin, are already fairly advanced clinically in human trials. For example, skin may be regenerated in vitro by taking skin cells from a donor, growing them up in tissue culture, and then transplanting back the expanded mass of skin back into a patient for therapeutic use (e.g., treatment of burns, ulcers, etc).

Further, the methods of the invention may be practiced using gene therapy. The recipient mammal's or patient's cells (which may be any type of cells but which are preferably fibroblasts or keratinocytes) can be engineered to express one or more of the subject growth factors, or combinations of GLP-2 with IGF-1 and/or IGF-2 and/or GH in vitro, followed by reimplantation, preferably in a capsule, in vivo for delivery of therapeutic amounts of these peptides. A variety of transfection techniques are currently available and used to transfer DNA in vitro into cells; including calcium phosphate-DNA precipitation, DEAE-Dextran transfection, electroporation, liposome-mediated DNA transfer or transduction with recombinant viral vectors. Such ex vivo treatment protocols have been proposed to transfer DNA into a variety of different cell types including epithelial cells (U.S. Pat. No. 4,868,116; Morgan and Mulligan WO87/00201; Morgan et al., 1987, Science 237:1476–1479; Morgan and Mulligan, U.S. Pat. No. 4,980,286); endothelial cells (WO89/05345); hepatocytes (WO89/07136; Wolff et al., 1987, Proc. Natl. Acad. Sci. USA 84:3344–3348; Ledley et al., 1987 Proc. Natl. Acad. Sci. 84:5335–5339; Wilson and Mulligan, WO89/07136; Wilson et al., 1990, Proc. Natl. Acad. Sci. 87:8437–8441); fibroblasts (Palmer et al., 1987, Proc. Natl. Acad. Sci. USA 84:1055–1059; Anson et al., 1987, Mol. Biol. Med. 4:11–20; Rosenberg et al., 1988, Science 242:1575–1578; Naughton & Naughton, U.S. Pat. No. 4,963,489); lymphocytes (Anderson et al., U.S. Pat. No. 5,399,346; Blaese, R. M., et al., 1995, Science 270:475–480); and hematopoietic stem cells (Lim, B., et al. 1989, Proc. Natl. Acad. Sci. USA 86:8892–8896; Anderson et al., U.S. Pat. No. 5,399,346).

It is expected that gene therapy is a viable method of providing growth hormones for the practice of the invention. Specifically, one can conduct an experiment in which cells from a cell line which secretes all the glucagon peptides are implanted into a mouse. The implanted cells grow as a tumor which secretes GLP-2 and induces growth of the small intestine. Since GLP-2 is the only glucagon derived peptide known to markedly stimulate small intestine growth, the effect on small intestine growth observed in this experiment was most likely due to the secretion of GLP-2. Similarly, cells may be engineered to produce GLP-2 alone, and/or at least one peptide hormone selected from the group consisting of IGF-1, IGF-2 and GH and implanted into a mammal.

Alternatively, one may use gene therapy to transfect in vivo the recipient's cells. Formulations of nucleic acid for such in vivo methods may include: naked DNA; nucleic acid encapsulated into liposomes or liposomes combined with viral envelope receptor proteins (Nicolau et al., 1983, Proc. Natl. Acad. Sci. USA 80:1068); DNA coupled to a polylysine-glycoprotein carrier complex; and nucleic acid precipitants. Nucleic acid preparations may be introduced in vivo using any one of the techniques known in the art such as direct injection, electroporation, and particle bombardment. In addition, "gene guns" have been used for gene delivery into cells (Australian Patent No. 9068389).

A related approach might involve the use of modified gene therapy and viral vectors encoding the gene products for GLP-2 and at least one other peptide hormone selected from the group consisting of IGF-1, IGF-2 and GH. Such viral vectors may be used to infect remnant intestinal epithelium in patients with intestinal compromise, thereby effecting targeted local therapeutic delivery of these substances to the intestine in vivo. However, it is not necessary for the practice of the invention that all cells are transformed, or even that intestinal cells be transformed. Indeed, cells in any tissue which can secrete the chosen hormone into the circulatory system, for example muscle cells, may be used to endogenously produce hormones.

The sequence of such DNAs for the practice of gene therapy methods can readily be determined from the amino acid sequences of the selected GLP-2, IGF-1, IGF-2 and GH with the limitation that only forms containing genetically encoded amino acids can be produced in this manner. Various expression vectors, including viral vectors, suitable for introduction of genetic information into human cells, can be employed and will incorporate the DNA's encoding GLP-2, IGF-1, IGF-2 and GH under expression controls functional in the host cells. Once altered genetically, the engineered cells can then be implanted using procedures established in the art.

The invention having been described, the following examples are offered by way of illustration and not limitation.

EXAMPLE 1

In this experiment, the effect of GLP-2 on cell proliferation of the mucosal epithelium and muscle layer of the esophagus was examined.

Female CD1 mice (6 weeks of age, approx. 25 g, Charles River) were housed in plastic bottom, wire lid cages and maintained on a 12 hr light/dark cycle and allowed chow and water ad libitum. The mice were weighed using a Mettler PJ300 scale and randomly allocated to either the control group (phosphate buffer saline injection ("PBS")) or the treatment group (human [Gly$^2$]GLP-2 injection). Each control or treatment group consisted of 2 mice housed together in 1 cage.

The female CD1 mice were treated (subcutaneously) with either human [Gly$^2$]GLP-2 2.5 μg or PBS alone, twice daily (8 a.m. and 6 p.m.) for 2 days prior to the bromodeoxyuridine ("BrdU") injection (50 ug/g body weight, in 0.5 ml). The mice received a total of 5 injections of either human [Gly$^2$]GLP-2 or saline over the previous 50 hours. Mice were fasted 21 hours before sacrifice. The mice were sacrificed 2 hours after receiving the BrdU injection. Upon sacrifice, sections of distal esophagus (the last 2 cm of esophagus adjacent to the gastroduodenal junction) were taken for histological analysis.

The esophageal tissues were fixed in 10% buffered formalin for over 24 hours and then placed in 70% alcohol prior to processing. Tissues were processed and embedded in paraffin using standard techniques. Four to six micron cross-sections were cut and stained with hematoxylin and eosin and a second set of slides were stained for BrdU-immunopositive cells. Intestinal micrometry was performed using the Leica Q500MC Image Analysis System. Results are shown in FIG. 1.

The results of this experiment clearly show that administration of human [Gly$^2$]GLP-2 over a 50 hr period produces significant increases in cellular proliferation of the mucosal epithelium and muscle layer of the esophagus as assessed by the number of BrDU-positive cells.

EXAMPLE 2

Figure 2:
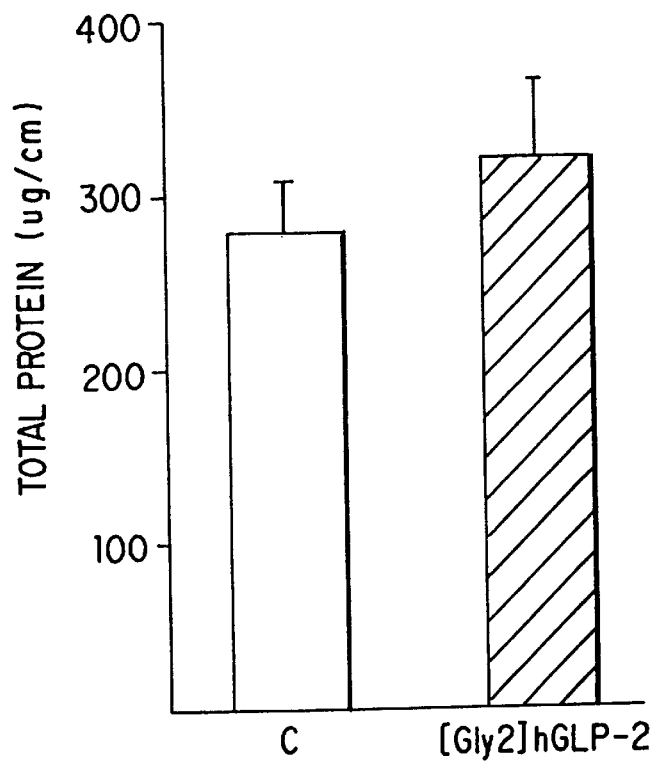
FIG. 2 illustrates the change in total protein content of the esophagus after treatment with GLP-2.

In this experiment, the effect of human [Gly$^2$]GLP-2 on protein synthesis in the mouse esophagus was examined. Female CD1 mice (6 weeks old) were housed and fed as described in Example 1. Two groups of mice (n=5 per group) were treated twice daily (subcutaneously) with either 0.5 ml PBS alone (control) or 2.5 ug in 0.5 ml PBS for 10 days. Following treatment, mice were anesthetized with $CO_2$ and sacrificed for analysis. One (1) cm segments of esophagus tissue, between 2–4 cm proximal to the gastroduodenal junction, were harvested for analysis of total cellular protein. The 1 cm esophageal segments were placed in 1 ml of PBS and homogenized using a Polytron. Aliquots of the homogenate were taken for protein determination of protein content using the modified Bradford assay (BIORAD). Results are shown in FIG. 2.

The protein content assay results show an increase in protein synthesis in the esophagus tissue following treatment with human [Gly$^2$]GLP-2. These results are consistent with the cellular action of human [Gly$^2$]GLP-2 on its target receptor in this tissue.

EXAMPLE 3

Figure 3:
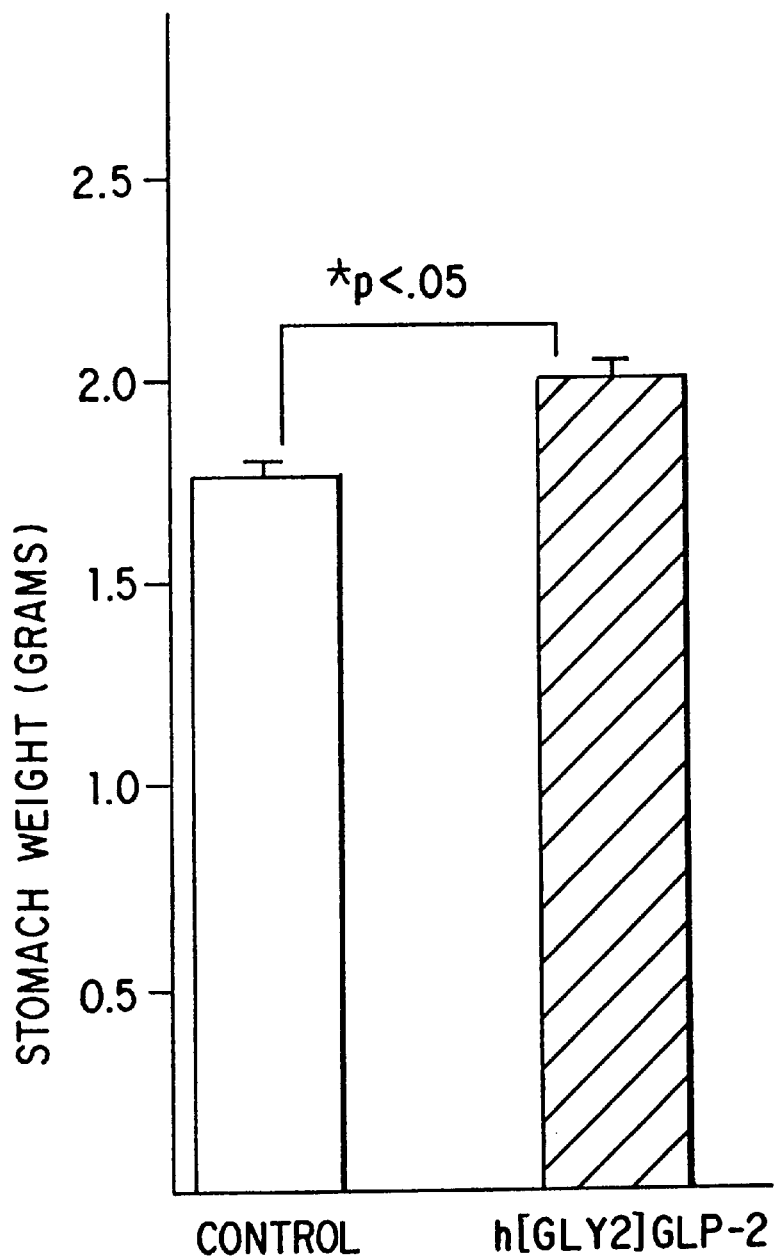
FIG. 3 illustrates the change in weight of the stomach after treatment with GLP-2.

In this experiment, the effect of GLP-2 on the stomach mass was examined. Female CD1 mice (6 weeks old) were treated with human [Gly$^2$]GLP-2 by oral administration in drinking water. The drinking water contained 4.3 μg/ml of human [Gly$^2$]GLP-2 and was prepared fresh daily. Each mouse received approximately 100 μg of human [Gly$^2$]GLP-2 per day. Following 12 days of treatment the mice were fasted for 24 hours, anesthetized with $CO_2$ and sacrificed. The stomach of each mouse was removed and weighed. Result are shown in FIG. 3.

The weights of the stomachs significantly increase with treatment of human [Gly$^2$] GLP-2 ($p<0.05$) as compared to control mice who received normal drinking water.

EXAMPLE 4

In this experiment, the prophylactic and therepeutic effect of GLP-2 on indomethacin induced mucosal epithelial damage was studied.

Nonsteroidal anti-inflammatory drugs (NSAIDs) are among the most commonly consumed medications in North America. Therapeutically, they have analgesic, anti-inflammatory, antipyretic, and antiplatelet properties. Gastrointestinal toxicity remains a major cause of morbidity despite attempts at prophylaxis using agents targeted at gastric acid suppression or via the administration of exogenous prostaglandins. Estimates of the incidence of NSAID-induced gastropathy, ranging from asymptomatic gastric erosions to life-threatening intestinal bleeds, varies between 15% and 20% in chronic NSAID users. The precise incidence of small intestinal damage (NSAID-induced enteropathy) remains unknown.

NSAIDs block the access of arachidonic acid to the binding site of cyclo-oxygenase (prostaglandin synthase) preventing the formation of prostaglandins and thromboxane. Suppression of prostaglandin synthesis, however, does not appear to be a major contributor to NSAID-induced small intestinal mucosal injury. Rather, alterations in epithelial permeability, increased luminal bacterial load, and bile contribute to epithelial injury. In rodents administered NSAIDs, in addition to gastropathy, small intestinal and colonic transmural inflammation and ulceration are noted, hence NSAID administration may be used to generate an animal model for inflammatory bowel disease.

GLP-2 administration to mice and rats stimulates mucosal growth in both the small and large intestine via activation of crypt cell proliferation and inhibition of enterocyte apoptosis. To address the possibility that GLP-2 may be useful for the therapeutic and/or prophylactic treatment of mucosal epithelial damage, we have studied the use of a novel human GLP-2 analog, h[Gly$^2$]-GLP-2, in mice with experimental indomethacin induced gastroenterocolitis.

Materials and Methods

Animals

Six to eight week old female CD1 mice (approximately 22–28 g, Charles River) were housed in plastic bottom, wire lid cages and maintained on a 12 hr light/dark cycle and allowed chow and water ad libitum throughout the study. The day prior to commencing the experiment, mice were weighed using a Mettler PJ300 scale and randomly allocated to a treatment group. Each treatment group consisted of 5 mice housed together. Subcutaneous injections of PBS or h[Gly$^2$]-GLP-2 peptide were given in the right hind quarter twice a day at 9 am and 7 pm. Injections started 4 days before indomethacin administration. Mice were fasted the night prior to receiving the first dose of indomethacin.

Mice were sacrificed between 9 am and 5 pm. Weight measurements were taken of the stomach, small intestine, and large intestine. Small and large bowel length were also measured. Blood was taken via cardiac puncture and the plasma isolated by centrifugation at 10,000 g for 10 minutes. Plasma was frozen at −70° C. for future analysis of GLP-2 levels. Tissues were removed for histological analysis, protein, wet and dry weight, RNA, and myeloperoxidase assay.

GLP-2 Administration 50.4 mg h[Gly$^2$]GLP-2 (ALX-0600) obtained from Allelix on Aug. 1, 1997 dissolved in sterile H$_2$O; 5N NaOH was used to pH the solution to a final pH 7. This batch of peptide was used for all experiments. Aliquots of 0.2, 0.5, 1.0, 2.0 mg/ml were frozen at −80° C. 600 µg of h[Gly$^2$]-GLP-2 in 1 ml solution was aliquoted into 399 ml phosphate buffer saline (PBS–137 mM NaCl, 2.7 mM KCl, 4.3 mM Na2HPO47H2O, 1.4 mM KH2PO4, pH 7.3) to obtain a final concentration of 1.5 ug/mL. 14 ml aliquots were stored at −80° C. and thawed in a 37° C. waterbath prior to injection. The injection volume was 0.5 ml per injection using ½ cc U-100 Insulin Syringes (Becton Dickinson and Company, NJ). Animals injected with PBS received the same PBS solution used to dilute the h[Gly$^2$]-GLP-2 peptide via an identical route of administration.

Indomethacin Administration

Indomethacin(1-[p-chlorobenzoyl]-5-methoxy-2-methylindole-3-acetic acic) (Sigma Chemical Co., St Louis MO, lot 74H1212), stock solution was prepared and aliquoted 1 hr before the first injection. The mice were weighed, and then fasted overnight, and given food one hour prior to the first indomethacin injection. Mice were not fasted for the second indomethacin injection. Indomethacin (14.5 mg) was weighed out using a Mettler AE166 scale and dissolved in 1 mL anhydrous ethyl alcohol. The solution was warmed at 37° C. for 5 minutes and thoroughly vortexed every minute until fully dissolved. 998.1 uL of stock indomethacin solution was diluted in 41 ml 5% NaHCO3 pH 7.3. Animals received 0.5 ml injections at 10:00 AM O.D. over two days. Indomethacin used in the second injection was stored at −20° C. overnight and allowed to thaw at room temperature prior to injection. Mice were injected at the same time (10:00 AM) on both days approximately 1 hr after receiving h[Gly$^2$]-GLP-2. Animals not receiving indomethacin were administered vehicle alone (250 µl anhydrous ethyl alcohol in 10.5 mL NaHCO3 pH 7.3 —a final injection volume of 0.5 ml was given daily over 2 days). Animals were sacrificed in a CO$_2$ chamber 14 days following the administration of either PBS or h[Gly$^2$]-GLP-2.

Results

Pilot experiments were performed to determine an indomethacin dose that reproducibly produced ~50% mortality in mice. For all groups receiving indomethacin treatment in this study, a dose of indomethacin 7 mg/kg administered s.c. bid for two days following overnight fasting was administered to 7–8 week old female CD1 mice. This dose consistently resulted in 50% mortality in saline-treated control animals. In each treatment group, subcutaneous injections of PBS or h[Gly$^2$]-GLP-2, 0.75 µg were administered twice daily to the animals receiving indomethacin and to the negative controls.

Treatment group I was used to characterize the type and extent of bowel injury produced by indomethacin (dose 7 mg/kg). Animals were pretreated with saline or h[Gly$^2$]-GLP-2 for 4 days, followed by an additional 2 days of either saline or h[Gly$^2$]-GLP-2 and indomethacin, then sacrificed two days following the initial indomethacin dose.

Treatment group II was used to examine the effect of four days of pretreatment with either h[Gly$^2$]-GLP-2 or saline followed by ten days of additional treatment with saline or h[Gly$^2$]-GLP-2.

Treatment group III was used to examine effects on mice treated with saline or h[Gly$^2$]-GLP-2 for 4 days prior and 2 days concurrent with indomethacin administration.

Treatment groups IV and V of the study involved mice receiving saline or h[Gly$^2$]-GLP-2 commencing concurrently (IV) or the day following (V) indomethacin administration and continued until the animals were sacrificed at the end of the day experimental period.

All h[Gly$^2$]-GLP-2-treated mice in groups II–V exhibited a marked increase in survival, ranging from 75–95%, in contrast with survival in saline-treated controls that ranged from 45–50%. This difference was highly statistically significant ($P<0.05$–$0.01$). Experimental endpoints included small and large bowel weights, histology, disease activity scores, mucosal enzyme activity, small and large bowel epithelial-specific gene expression, markers of the inflammatory response such as expression of cytokines and myeloperoxidase and GLP-2 content. The majority of parameters assessed, especially markers of epithelial damage/inflammation, were significantly improved in the h[Gly$^2$]-GLP-2-treated mice.

EQUIVALENTS

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

What is claimed is:

1. A method for treating a subject in need of such treatment to enhance functioning of the upper gastrointestinal tract including the esophagus and the stomach, comprising the step of delivering to the upper gastrointestinal tract of the subject a GLP-2 receptor agonist in an amount effective to enhance functioning of the upper gastrointestinal tract.

2. A method for treating a subject to enhance functioning of the upper gastrointestinal tract according to claim 1, wherein GLP-2 or a peptidic analog of GLP-2 is delivered to the esophagus.

3. A method for treating a subject to enhance functioning of the upper gastrointestinal tract according to claim 1, wherein GLP-2 or a peptidic analog of GLP-2 is delivered to the stomach.

4. A method of treating a subject in need of such treatment to proliferate the tissue of the upper gastrointestinal tract, comprising the step of delivering to the upper gastrointestinal tract of the subject GLP-2 or a peptidic analog of GLP-2, in an amount effective to proliferate the tissue of the upper gastrointestinal tract.

5. The method according to claim 4, wherein the subject is suffering from an inflammatory condition involving the upper gastrointestinal tract.

6. The method according to claim 5, wherein the inflammatory condition involving the upper gastrointestinal tract is an inflammatory condition involving the esophagus.

7. The method according to claim 6, wherein the inflammatory condition involving the esophagus is selected from the group consisting of inflammation-vasculitis, post-infection inflammation, infiltrative disorder, infectious esophagitis, non-infectious esophagitis, sarcoidosis, Crohn's disease, Behcet's disease, graft-versus-host disease, acid reflux, bile reflux, drug-induced injury, chemical injury, radiation, myositis and collagen vascular diseases.

8. The method according to claim 5, wherein the inflammatory condition involving the upper gastrointestinal tract is an inflammatory condition involving the stomach.

9. The method according to claim 8, wherein the inflammatory condition involving the stomach is selected from the group consisting of hemorrhagic and erosive gastritis, Helicobacter pylori gastritis, chemical gastritis, metaplastic atrophic gastritis, postantrectomy atrophic gastritis, eosinophilic gastritis, infectious gastritis, Crohn's disease, sarcoidosis, isolated granulomatous gastritis, lymphocytic gastritis, and Ménétriere's disease.

10. The method according to claim 4, wherein the subject has undergone partial or subtotal resection of the upper gastrointestinal tract.

11. The method according to claim 10, wherein the partial or total resection of the upper gastrointestinal tract involves the esophagus or the stomach.

12. The method according to claim 4, wherein the subject is a human.

13. The method according to claim 12, wherein the analog of GLP-2 has enhanced upper gastrointestinal tract cell proliferating activity relative to native rat GLP-2.

14. The method according to claim 13, wherein the analog of GLP-2 is human [Gly$^2$]GLP-2.

15. The method according to claim 14, wherein the analog of GLP-2 is delivered to the upper gastrointestinal tract by oral, subcutaneous, or intravenous administration.

16. A method to identify peptides useful to treat inflammatory conditions involving the upper gastrointestinal tract, comprising the steps of:
   a) obtaining an analog of a vertebrate GLP-2 peptide, the analog having at least one amino acid substitution, deletion, addition, or an amino acid with a blocking group;
   b) inducing an inflammatory condition involving the upper gastrointestinal tract in a test animal;
   c) treating the test animal having an induced inflammatory condition of the upper gastrointestinal tract, with the analog using a regimen capable of eliciting an amelioration of the inflammatory condition of the upper gastrointestinal tract when utilized for native GLP-2; and
   d) determining the effect of the analog on the health status or mortality of the test animal compared with control animals not receiving the peptide or determining the effect of the analog on the weight of the upper gastrointestinal tract of test animals compared to control animals not receiving peptide.

17. A method to identify peptides useful to prevent or ameliorate inflammatory conditions involving the upper gastrointestinal tract, comprising the steps of:
   a) obtaining an analog of a vertebrate GLP-2 peptide, the analog having at least one amino acid substitution, deletion, addition, or an amino acid with a blocking group;
   b) treating a test animal having an induced inflammatory condition of the upper gastrointestinal tract, with the analog using a regimen capable of eliciting an amelioration of the inflammatory condition of the upper gastrointestinal tract when utilized for native GLP-2;
   c) inducing an inflammatory condition involving the upper gastrointestinal tract in a test animal; and
   d) determining the effect of the analog on the health status or mortality of the test animal compared with control animals not receiving the peptide or determining the effect of the analog on the weight of the upper gastrointestinal tract of test animals compared to control animals not receiving peptide.

18. A method useful to identify peptides capable of proliferating tissue of the upper gastrointestinal tract, comprising the steps of:
   a) obtaining an analog of a vertebrate GLP-2 peptide, the analog having at least one amino acid substitution, deletion, addition, or an amino acid with a blocking group;
   b) delivering the analog to the upper gastrointestinal tract of the test animal using a regimen capable of eliciting proliferation of the upper gastrointestinal tract when utilized for native GLP-2; and
   c) assessing the increase in the mass, length, or total protein content of the upper gastrointestinal tract or representative portion after completion of the treatment regimen.

19. A method of prophylactically treating a subject at risk of developing an inflammatory condition involving inflammation of the upper gastrointestinal tract, the method comprising:
   a) identifying a subject at risk of developing inflammatory condition involving the upper gastrointestinal tract; and
   b) administering to the subject an amount of GLP-2 or a GLP-2 analog demonstrated to inhibit onset and/or ameliorate the development of the inflammatory condition.

20. A method of promoting the growth of upper gastrointestinal tract tissue in a mammal, comprising administering to the mammal GLP-2, or an analog of GLP-2, and at least one other peptide hormone selected from the group consisting of IGF-1, analogs of IGF-1, IGF-2, analogs of IGF-2, GH, and analogs of GH.

21. The method according to claim 20 comprising co-administering to a mammal an effective amount of GLP-2, or an analog of GLP-2, and an effective amount of at least one other peptide hormone selected from the group consisting of IGF-1, analogs of IGF-1, IGF-2, analogs of IGF-2, GH, and analogs of GH.

22. The method according to claim 20 comprising implanting cells into the mammal, wherein the cells have been genetically engineered ex vivo to produce GLP-2 and/or the other peptide hormone.

23. The method according to claim 20 comprising genetically engineering cells of the mammal in vivo to produce GLP-2 and/or the other peptide hormone.

24. The method according to claim 20 wherein the peptide hormone is IGF-1 or LRIGF-1.

25. The method according to claim 20 wherein the peptide hormone is IGF-2.

26. The method according to claim 20 wherein the peptide hormone is GH.

27. The method according to claim 20 for promoting the growth of the esophagus.

28. The method according to claim 20 for promoting the growth of the stomach.

29. A method for treating a subject to enhance functioning of the upper gastrointestinal tract, comprising administering to the subject GLP-2, or an analog of GLP-2, and at least one other peptide hormone selected from the group consisting of IGF-1, analogs of IGF-1, IGF-2, analogs of IGF-2, GH, analogs of GH, EGF, analogs of EGF, HGF, analogs of HGF, KGF, and analogs of KGF.

30. The method according to claim 29 for preserving, restoring or maintaining upper gastrointestinal tract function:
   after a regimen of chemotherapy or radiotherapy;
   after a period of parenteral nutrition;
   after gastrointestinal disease; or
   wherein said subject is a premature infant.

31. The method according to claim 29, wherein the subject is suffering from an inflammatory condition involving the upper gastrointestinal tract.

32. The method according to claim 31, wherein the inflammatory condition involving the upper gastrointestinal tract is an inflammatory condition involving the esophagus.

33. The method according to claim 32, wherein the inflammatory condition involving the esophagus is selected from the group consisting of inflammation-vasculitis, post-infection inflammation, infiltrative disorder, infectious esophagitis, non-infectious esophagitis, sarcoidosis, Crohn's disease, Behcet's disease, graft-versus-host disease, acid reflux, bile reflux, drug-induced injury, chemical injury, radiation, myositis and collagen vascular diseases.

34. The method according to claim 31, wherein the inflammatory condition involving the upper gastrointestinal tract is an inflammatory condition involving the stomach.

35. The method according to claim 34, wherein the inflammatory condition involving the stomach is selected from the group consisting of hemorrhagic and erosive gastritis, *Helicobacter pylori* gastritis, chemical gastritis, metaplastic atrophic gastritis, postantrectomy atrophic gastritis, eosinophilic gastritis, infectious gastritis, Crohn's disease, sarcoidosis, isolated granulomatous gastritis, lymphocytic gastritis, and Menetriere's disease.

36. The method according to claim 29, wherein the subject has undergone partial or subtotal resection of the upper gastrointestinal tract.

37. The method according to claim 36, wherein the partial or total resection of the upper gastrointestinal tract involves the esophagus or the stomach.

38. The method according to claim 29, wherein the subject is a human.

39. The method according to claim 38, wherein the analog of GLP-2 has enhanced upper gastrointestinal tract cell proliferating activity relative to native rat GLP-2.

40. The method according to claim 39, wherein the analog of GLP-2 is human [Gly$^2$] GLP-2.

41. The method according to claim 40, wherein the analog of GLP-2 is delivered to the upper gastrointestinal tract by oral, subcutaneous, or intravenous administration.

42. A kit comprising GLP-2 and at least one other peptide hormone selected from the group consisting of IGF-1, IGF-2, GH, EGF, HGF and KGF in a therapeutically effective unit dose or multi-dose amount.

43. A method for promoting the growth of upper gastrointestinal tract tissue or cells which comprises the step of culturing said tissue or cells in a culturing medium containing a growth promoting combination of both GLP-2, or an analog of GLP-2, and at least one other peptide hormone selected from the group consisting of IGF-1, analogs of IGF-1, IGF-2, analogs of IGF-2, GH, analogs of GH, EGF, analogs of EGF, HGF, analogs of HGF, KGF, and analogs of KGF.

44. A method in which treatment of a patient to restore the upper gastrointestinal tract is performed by the steps of:
(a) culturing tissue or cells derived from the patient with a tissue growth promoting amount of a combination of GLP-2, or an GLP-2 analog, and at least one other peptide hormone selected from the group consisting of IGF-1, analogs of IGF-1, IGF-2, analogs of IGF-2, GH, analogs of GH, EGF, analogs of EGF, HGF, analogs of HGF, KGF, and analogs of KGF, and
(b) implanting said tissue or cells in the patient to be treated.

45. A method for determining the activity of a hormone when used in combination with GLP-2, said method comprising the steps of:
(a) coadministering the hormone with an amount of GLP-2, or an GLP-2 analog, to a test mammal,
(b) assessing the subsequent growth of upper gastrointestinal tract tissue in the test mammal, and
(c) determining whether the growth of upper gastrointestinal tract tissue in the test mammal is enhanced relative to control mammals treated with GLP-2 alone.

46. A method for treating a subject having peptidic ulcers comprising the step of delivering to the upper gastrointestinal tract of the subject GLP-2, or an analog of GLP-2, and at least one other agent effective for treating peptidic ulcers selected from the group consisting of: agents that act to block acid secretion from the stomach, agents that act to form a protective barrier in the stomach, and bismuth containing compounds, in an effective therapeutic amount.

47. The method according to claim 46 wherein the agents that act to block acid secretion from the stomach include $H_2$ receptor antagonists, proton pump inhibitors and prostaglandins.

48. The method according to claim 46 wherein the agents that act to form a protective barrier in the stomach includes sucralfate.

* * * * *

SEQUENCE LISTING

```
<160> NUMBER OF SEQ ID NOS: 2

<210> SEQ ID NO 1
<211> LENGTH: 33
<212> TYPE: PRT
<213> ORGANISM: HUMAN
```

-continued

```
<400> SEQUENCE: 1

His Ala Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 33
<212> TYPE: PRT
<213> ORGANISM: RAT

<400> SEQUENCE: 2

His Ala Asp Gly Ser Phe Ser Asp Glu Met Asn Thr Ile Leu Asp Asn
 1               5                  10                  15

Leu Ala Thr Arg Asp Phe Ile Asn Trp Leu Ile Gln Thr Lys Ile Thr
            20                  25                  30

Asp
```